(12) United States Patent
Higashi

(10) Patent No.: US 9,679,109 B2
(45) Date of Patent: Jun. 13, 2017

(54) INTERVIEW SYSTEM, SERVER SYSTEM, SERVER DEVICE, INFORMATION TERMINAL, INTERVIEW METHOD, INFORMATION PROCESSING METHOD, AND PROGRAM

(71) Applicant: Haruomi Higashi, Kanagawa (JP)

(72) Inventor: Haruomi Higashi, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 14/982,168

(22) Filed: Dec. 29, 2015

(65) Prior Publication Data

US 2016/0196402 A1    Jul. 7, 2016

(30) Foreign Application Priority Data

Jan. 6, 2015   (JP) ................. 2015-000717

(51) Int. Cl.
*H04N 7/14* (2006.01)
*G06F 19/00* (2011.01)
*G06F 3/14* (2006.01)

(52) U.S. Cl.
CPC ............ *G06F 19/3418* (2013.01); *G06F 3/14* (2013.01); *H04N 7/147* (2013.01)

(58) Field of Classification Search
CPC ............ H04N 7/14; H04N 4/141; H04N 1/42; H04N 7/147; H04N 21/4788; H04N 7/144; H04N 7/15; H04N 7/155; H04M 2201/50; H04M 3/567; G06F 19/3425; G06F 19/3418; G06F 19/3431
(Continued)

(56) References Cited

U.S. PATENT DOCUMENTS 5,544,649 A * 8/1996 David ................. A61B 5/6887
                                                     128/904
2005/0182302 A1* 8/2005 Johnson ............... A61B 5/0002
                                                     600/300
(Continued)

FOREIGN PATENT DOCUMENTS

JP    2002-224053    8/2002
JP    2010-262384    11/2010

*Primary Examiner* — Stella Woo
(74) *Attorney, Agent, or Firm* — Harness, Dickey & Pierce, P.L.C.

(57) ABSTRACT

An information processing system includes one or more information processing devices and controls bidirectional communication of image data and audio data between a first information terminal used by a first user and a second information terminal used by a second user. The information processing system includes a calculation unit analyzing the image data and the audio data on the second user received from the second information terminal and calculating difference information that indicates a difference between a current state and a past state of the second user; an image generation unit superimposing the difference information on the image data received from the second information terminal, such that the difference information is displayed around a field where an image of the second user is placed; and a transmission unit transmitting, to the first information terminal, the image data on which the difference information is superimposed and the audio data.

12 Claims, 25 Drawing Sheets

(58) Field of Classification Search
 USPC ............ 348/14.01–14.16; 382/128; 709/204
 See application file for complete search history.

(56) References Cited

U.S. PATENT DOCUMENTS

2005/0276392 A1* 12/2005 Berenguer ............ H04N 7/147
 379/88.13
2008/0292151 A1* 11/2008 Kurtz ........................ A61B 3/10
 382/128
2014/0232814 A1* 8/2014 Malhotra ................ H04N 7/15
 348/14.07

* cited by examiner

FIG.5

| BASIC INFORMATION SECTION ||||
|---|---|---|---|
| NAME | | AGE | |
| SEX | | EMPLOYEE NUMBER | |
| YEAR OF ENTERING COMPANY | | DEPARTMENT | |

| MEDICAL EXAMINATION INFORMATION SECTION ||||
|---|---|---|---|
| ITEM \ YEAR | 2012 | 2013 | 2014 |
| HEIGHT | | | |
| WEIGHT | | | |
| SUBJECTIVE SYMPTOM | | | |
| AMOUNT OF TOBACCO | | | |
| AMOUNT OF ALCOHOL | | | |
| FREQUENCY OF EXERCISE | | | |
| MEAL CONDITION | | | |
| NAME OF DISEASE, FOLLOW-UP OBSERVATION | | | |
| HISTORY OF HOSPITALIZATION | | | |
| FAMILY MEDICAL HISTORY | | | |

| BASIC INFORMATION SECTION ||||
| NAME | | AGE | |
| SEX | | EMPLOYEE NUMBER | |
| YEAR OF ENTERING COMPANY | | DEPARTMENT | |
| WORKING INFORMATION SECTION ||||
| 2014 ||||
| JANUARY || FEBRUARY ||
| 1 (WED.) | | 1 (MON.) | 9:10-17:05 |
| 2 (THURS.) | | 2 (TUE.) | 8:55-17:05 |
| 3 (FRI.) | | 3 (WED.) | 8:54-17:01 |
| 4 (SAT.) | | 4 (THURS.) | 8:57-17:15 |
| 5 (SUN.) | | 5 (FRI.) | 8:55-17:02 |
| 6 (MON.) | 8:55-17:05 | 6 (SAT.) | |
| 7 (TUE.) | 8:54-17:01 | 7 (SUN.) | |
| 8 (WED.) | 8:57-17:15 | 8 (MON.) | 9:15-17:10 |
| 9 (THURS.) | 8:55-17:02 | 9 (TUE.) | 8:55-17:05 |

| ID | QUESTIONS | DISPLAY CONDITIONS | | | | |
|---|---|---|---|---|---|---|
| | | LACK OF SLEEP | OBESITY | INCREASED STRESS | INCREASED DRINKING OF ALCOHOL | DEPRESSIVE TENDENCY |
| 1 | CAN YOU EASILY TAKE A DAY OFF? | ○ | | | | ○ |
| 2 | HOW DO YOU SPEND YOUR LUNCHTIME? | ○ | | | | |
| 3 | DO YOU OFTEN EAT BETWEEN MEALS? | | ○ | | | |
| 4 | WHAT DO YOU DO FOR RECREATION? | | ○ | ○ | | ○ |
| 5 | HOW OFTEN DO YOU EXERCISE? | | ○ | ○ | | |
| 6 | HOW OFTEN DO YOU DRINK ALCOHOL? | | | | ○ | |
| ⋮ | ⋮ | | | | | |

FIG.8

| ID | ADVICE | DISPLAY CONDITIONS ||||| 
| | | LACK OF SLEEP | OBESITY | INCREASED STRESS | INCREASED DRINKING OF ALCOHOL | DEPRESSIVE TENDENCY |
|---|---|---|---|---|---|---|
| 1 | TAKE A RECOMMENDED AMOUNT OF SLEEP (7 HOURS OR MORE). | ○ | | | | ○ |
| 2 | TAKE A NAP FOR AT LEAST 15 MINUTES AT LUNCHTIME. | ○ | | | | |
| 3 | TAKE A BALANCED DIET WHILE QUITTING BETWEEN MEALS. | | ○ | | | |
| 4 | GO OUT FOR RECREATION ON HOLIDAYS. | | ○ | ○ | | ○ |
| 5 | EXERCISE AT LEAST ONCE A WEEK. | | ○ | ○ | | |
| 6 | DO NOT KEEP ALCOHOL AT HOME. | | | | ○ | |
| ... | ... | | | | | |

FIG.9A

| BASIC INFORMATION SECTION ||||||
|---|---|---|---|---|---|
| NAME || | AGE ||||
| SEX || | EMPLOYEE NUMBER ||||
| YEAR OF ENTERING COMPANY || | DEPARTMENT ||||
| IMAGE INFORMATION SECTION ||||||
| ITEM || DATE OF MEASUREMENT | FEBRUARY 3, 2014 | MAY 23, 2014 | AUGUST 11, 2014 |
| PULSE RATE OR HEARTBEAT |||||||
| FACIAL EXPRESSION | ANGER ||||
| | CONTEMPT ||||
| | DISLIKE ||||
| | UNEASINESS ||||
| | JOY ||||
| | SORROW ||||
| | SURPRISE ||||
| | NEUTRALITY ||||
| SENTIMENT | COLOR OF FACE ||||
| | COLOR OF LIPS ||||
| BEHAVIOR | HEAD MOVEMENT ||||
| | BODY MOVEMENT ||||
| | LIP MOVEMENT ||||
| | EYE MOVEMENT ||||
| APPEARANCE | COLOR OF HAIR ||||
| | HAIRSTYLE ||||
| | CLOTHES ||||
| IMAGE DATA || V001 | V002 | V003 |

FIG.9B

| BASIC INFORMATION SECTION |||| |
|---|---|---|---|
| NAME | | AGE | |
| SEX | | EMPLOYEE NUMBER | |
| YEAR OF ENTERING COMPANY | | DEPARTMENT | |
| AUDIO INFORMATION SECTION |||| |
| ITEM | DATE OF MEASUREMENT | FEBRUARY 3, 2014 | MAY 23, 2014 | AUGUST 11, 2014 |
| CONVERSATION | TONE | | | |
| | NUMBER OF SPEECHES /SPEECH PERIOD | | | |
| | NUMBER OF SILENCES /SILENCE PERIOD | | | |
| | NEGATIVE EXPRESSION | | | |
| AUDIO DATA || A001 | A002 | A003 |

| BASIC INFORMATION SECTION |||||
|---|---|---|---|---|
| NAME | | AGE | | |
| SEX | | EMPLOYEE NUMBER | | |
| YEAR OF ENTERING COMPANY | | DEPARTMENT | | |
| GRAPH INFORMATION SECTION |||||
| ITEM \ DATE OF MEASUREMENT | | FEBRUARY 3, 2014 | MAY 23, 2014 | AUGUST 11, 2014 |
| BECAME LESS ENERGETIC | | | | |
| BECAME MENTALLY UNSTABLE | | | | |
| BECAME LESS INTERESTED IN APPEARANCES | | | | |
| BECAME TACITURN SUDDENLY | | | | |
| MADE COMPLAINTS | | | | |
| LOST (GAINED) WEIGHT SUDDENLY | | | | |
| INCREASED AMOUNT OF ALCOHOL | | | | |
| INCREASED NUMBER OF LATE ARRIVALS AND ABSENCE | | | | |

| FACIAL EXPRESSION PARAMETERS | TIME PASSED DURING INTERVIEW | | | | | | | TOTAL |
|---|---|---|---|---|---|---|---|---|
| | 5 | 10 | 15 | 20 | 25 | 30 | | |
| ANGER | 1 | 2 | 3 | 0 | 0 | 0 | | 6 |
| CONTEMPT | 2 | 4 | 2 | 1 | 0 | 0 | | 9 |
| DISLIKE | 10 | 6 | 4 | 2 | 0 | 1 | | 23 |
| UNEASINESS | 8 | 10 | 12 | 6 | 4 | 2 | | 42 |
| JOY | 0 | 0 | 1 | 4 | 8 | 7 | | 20 |
| SORROW | 1 | 5 | 4 | 2 | 0 | 0 | | 12 |
| SURPRISE | 0 | 4 | 7 | 6 | 6 | 1 | | 24 |
| NEUTRALITY | 16 | 10 | 8 | 18 | 21 | 17 | | 90 |

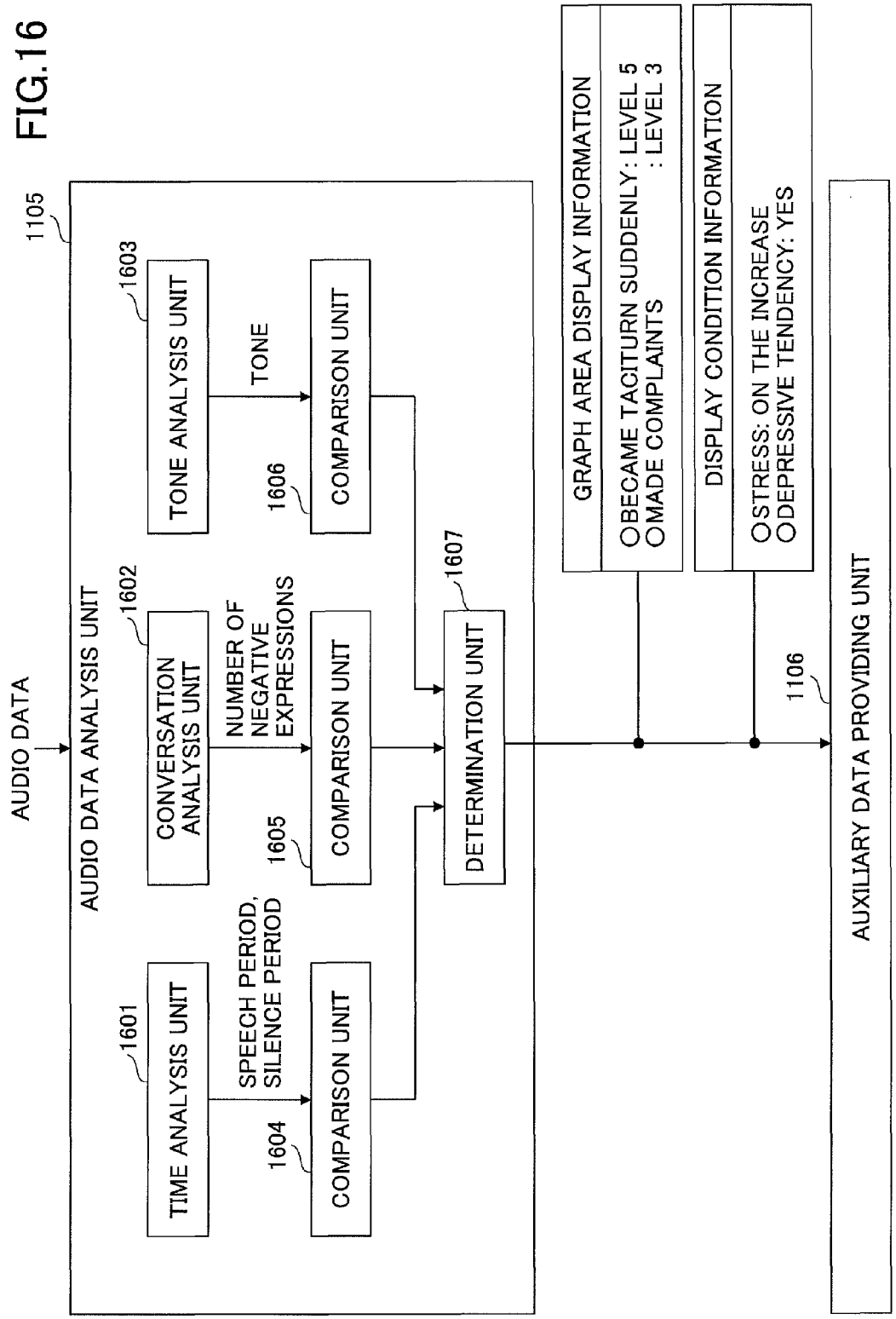

FIG.17A

| INTERVIEW DATE: APRIL 1, 2014 | | | | | | | | |
|---|---|---|---|---|---|---|---|---|
| TIME STAMP | ... | 0:01:05 | 0:01:10 | 0:01:16 | 0:01:20 | 0:01:28 | 0:01:36 | 0:01:38 | 0:01:45 |
| INTERVIEWEE | | SPEECH: 5 SECONDS | | SILENCE: 4 SECONDS | | SPEECH: 17 SECONDS | | ... |
| HEALTHCARE PROFESSIONAL | | | SPEECH: 6 SECONDS | | SILENCE: 16 SECONDS | | SPEECH: 7 SECONDS | ... |

FIG.17B

| INTERVIEW DATE: OCTOBER 1, 2014 | | | | | | | | |
|---|---|---|---|---|---|---|---|---|
| TIME STAMP | ... | 0:01:05 | 0:01:10 | 0:01:16 | 0:01:20 | 0:01:28 | 0:01:36 | 0:01:38 | 0:01:45 |
| INTERVIEWEE | | SPEECH: 40 SECONDS | | | | | | ... |
| HEALTHCARE PROFESSIONAL | | | SPEECH: 6 SECONDS | | SILENCE: 16 SECONDS | | SPEECH: 7 SECONDS | ... |

FIG.17C

| INTERVIEWEE | SPEECH PERIOD (min.) | SILENCE PERIOD (min.) |
|---|---|---|
| APRIL 1, 2014 | 7 | 23 |
| OCTOBER 1, 2014 | 23 | 7 |
| DIFFERENCE (min.) | 16 | −16 |

INTERVIEW SYSTEM, SERVER SYSTEM, SERVER DEVICE, INFORMATION TERMINAL, INTERVIEW METHOD, INFORMATION PROCESSING METHOD, AND PROGRAM

BACKGROUND OF THE INVENTION

Field of the Invention

The present invention relates to an interview system, a server system, a server device, an information terminal, an interview method, an information processing method, and a program.

Description of the Related Art

There are medical interview systems in which a healthcare professional such as a doctor holds a medical interview with an interviewee in a remote place (in order to comprehend a health condition of the interviewee). The medical interview systems refer to systems in which an information terminal of the healthcare professional and an information terminal in the remote place are connected via a network and bidirectional communication is performed using images and audio, so that a medical interview with the interviewee is conducted.

If this medical interview system is used, it is possible to communicate in a virtual face-to-face state. The healthcare professional can comprehend the health condition of the interviewee in the remote place through facial expression, complexion, behavior, a state of speech, and the like of the interviewee and can provide advice where necessary.

By contrast, if the healthcare professional is to provide appropriate advice in a medical interview, it is necessary to consider each piece of past information about the interviewee during the medical interview by comparing past data on the interviewee (data on past medical interviews and results of medical examinations) with corresponding current states, for example.

However, if the healthcare professional faces a direction different from a direction of the interviewee (namely, photographing direction) while working in order to consider the past information about the interviewee, communication in a virtual face-to-face state is interrupted. As a result, the interviewee may experience inconvenience such as alienation.

[Patent Document 1] Japanese Laid-Open Patent Application No. 2002-224053

SUMMARY OF THE INVENTION

It is a general object of at least one embodiment of the present invention to provide an interview system capable of maintaining communication in a virtual face-to-face state.

An information processing system includes one or more information processing devices and controls bidirectional communication of first image data, second image data, first audio data, and second audio data between a first information terminal used by a first user and a second information terminal used by a second user. The information processing system includes a calculation unit that analyzes the second image data and the second audio data on the second user received from the second information terminal and calculates difference information that indicates a difference between a current state of the second user and a past state of the second user; an image generation unit that superimposes the difference information on the second image data received from the second information terminal, such that the difference information is displayed around a field where an image of the second user is placed; and a transmission unit that transmits, to the first information terminal, the second image data on which the difference information is superimposed by the image generation unit and the second audio data received from the second information terminal.

According an embodiment of the present invention, it is possible to provide an interview system capable of maintaining communication in a virtual face-to-face state.

BRIEF DESCRIPTION OF THE DRAWINGS

Other objects and further features of embodiments will become apparent from the following detailed description when read in conjunction with the accompanying drawings, in which:

FIG. 5 is a diagram showing a group of medical examination information sections;

FIG. 6 is a diagram showing a group of working information sections;

FIG. 7 is a diagram showing question information;

FIG. 8 is a diagram showing advice information;

FIG. 9A is a diagram showing first obtained information;

FIG. 9B is a diagram showing second obtained information;

FIG. 10 is a diagram showing graph information;

FIG. 16 is a diagram illustrating a process of an audio data analysis unit;

FIG. 17A is a diagram schematically showing a speech period and a silence period of an interviewee and a speech period and a silence period of a healthcare professional during a medical interview;

FIG. 17B is a diagram schematically showing a speech period and a silence period of an interviewee and a speech period and a silence period of a healthcare professional during a medical interview;

FIG. 17C is a diagram showing a difference of a speech period and a silence period of an interviewee;

DESCRIPTION OF THE PREFERRED EMBODIMENTS

Figure 1:
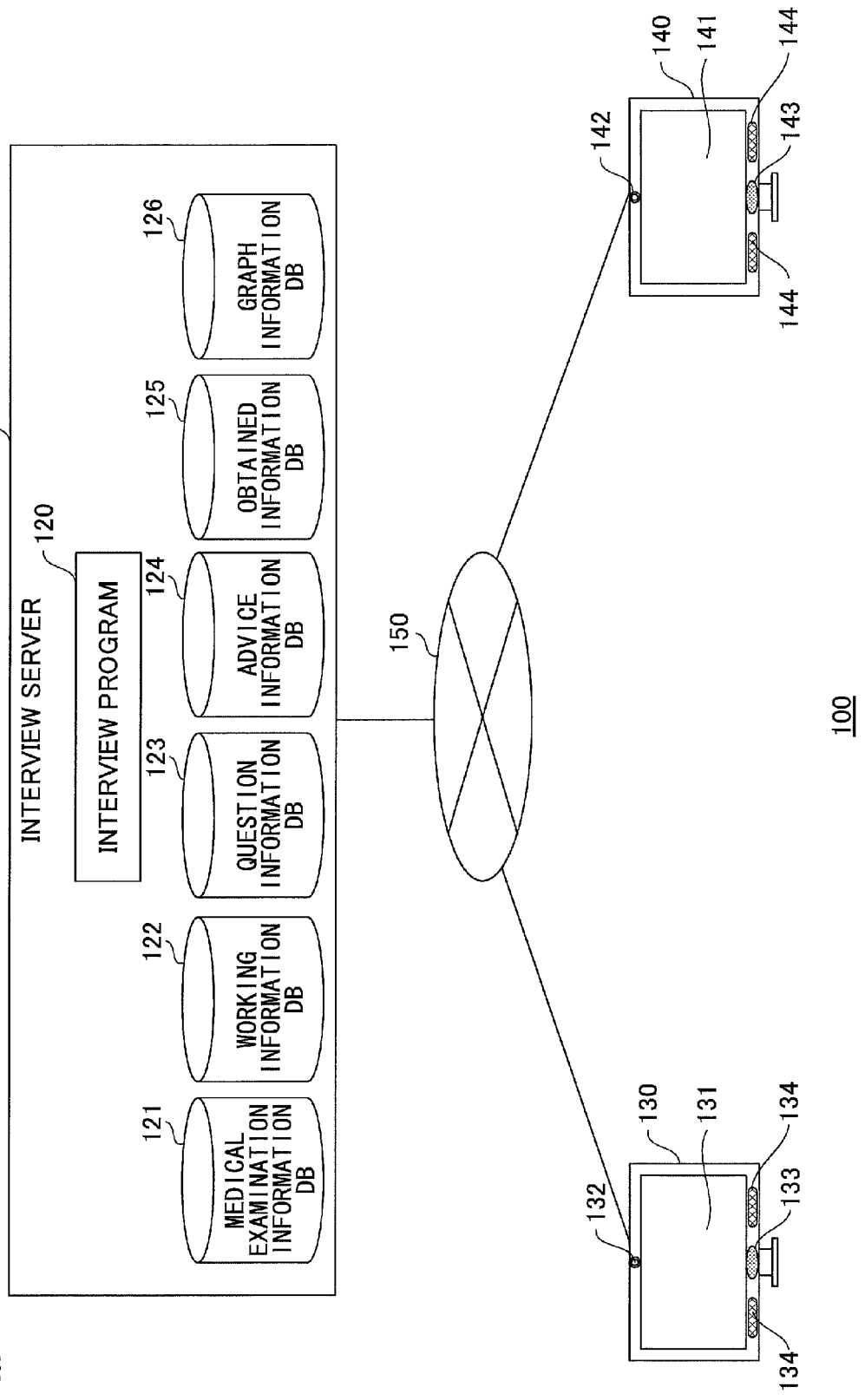
FIG. 1 is a diagram showing an entire configuration of a medical interview system.

In the following, embodiments of the present invention will be described with reference to the drawings. In descriptions and drawings of the embodiments, constituent elements having substantively the same functional configurations are provided with the same reference numerals and a repetitive description will be omitted.

First Embodiment

<1. Entire Configuration of Medical Interview System>

First, an entire configuration of a medical interview system will be described. FIG. 1 is a diagram showing an entire configuration of a medical interview system.

As shown in FIG. 1, a medical interview system 100 includes an interview server 110, an information terminal 130, and an information terminal 140. The interview server 110, the information terminal 130, and the information terminal 140 are communicatively connected via a network 150.

The interview server 110 is a server device that controls bidirectional communication of image data and audio data between the information terminal 130 and the information terminal 140. The interview server 110 includes an interview program 120, a medical examination information database (hereafter "DB") 121, a working information DB 122, a question information DB 123, an advice information DB 124, an obtained information DB 125, and a graph information DB 126.

The interview program 120 controls a medical interview process for conducting a medical interview (to comprehend a health condition of an interviewee, for example) between a healthcare professional (interviewer) such as a doctor with the interviewee in a remote place via the information terminal 130. The present embodiment is described based on the assumption that the healthcare professional that uses the interview program 120 is an industrial physician. Further, the present embodiment is described on the assumption that the interviewee in the remote place is an employee of a company that the industrial physician contracts with.

The medical examination information DB 121 stores medical examination information about an interviewee. The working information DB 122 stores working information that indicates actual working conditions of the interviewee in a company.

The question information DB 123 stores question information including questions to ask the interviewee in order to more accurately comprehend a state of the interviewee. The question information has conditions provided to automatically select a question from a plurality of questions depending on the interviewee. In accordance with this, the healthcare professional can ask a question suitable for the interviewee.

The advice information DB 124 stores advice information including pieces of advice to improve the state of the interviewee. The advice information has conditions provided to automatically select a piece of advice from a plurality of pieces of advice depending on the state of the interviewee. In accordance with this, the healthcare professional can give advice suitable for the interviewee.

The obtained information DB 125 stores, for each day of a medical interview conducted, image data and audio data on the interviewee obtained during the medical interview and information indicating the state of the interviewee, the information being derived through an analysis of the obtained image data and audio data on the interviewee.

The graph information DB 126 stores, for each day of a medical interview conducted, graph information to express using a graph, the graph information being derived based on information that indicates the state of the interviewee and showing a part of information that indicates a difference from a past state of the interviewee.

The information terminal 130 is a terminal used by a healthcare professional such as a doctor when a medical interview is conducted. The information terminal 130 includes an imaging unit 132 that faces a display direction of a display screen 131 as a photographing direction thereof. In accordance with this, it is possible to photograph the front of the healthcare professional seated in a location that faces the display screen 131. Further, the information terminal 130 includes a microphone unit 133 that obtains voice uttered by the healthcare professional and a loudspeaker unit 134 that outputs audio to the healthcare professional.

The information terminal 140 is a terminal used by an interviewee when a medical interview is conducted. The information terminal 140 includes an imaging unit 142 that faces a display direction of a display screen 141 as a photographing direction thereof. In accordance with this, it is possible to photograph the front of the interviewee seated in a location that faces the display screen 141. Further, the information terminal 140 includes a microphone unit 143 that obtains voice uttered by the interviewee and a loudspeaker unit 144 that outputs audio to the interviewee.

FIG. 1 shows a case where a single interview server 110 executes the interview program 120. However, a part of the interview program 120 may be executed by another server. Further, in FIG. 1, the single interview server 110 includes the medical examination information DB 121, the working information DB 122, the question information DB 123, the advice information DB 124, the obtained information DB 125, and the graph information DB 126. However, each of the medical examination information DB 121, the working information DB 122, the question information DB 123, the advice information DB 124, the obtained information DB 125, and the graph information DB 126 may be included in different servers.

In other words, the medical interview system 100 may be configured as a "server system" including a plurality of servers.

<2. Use of Medical Interview System and Flow of Data>

Figure 2:
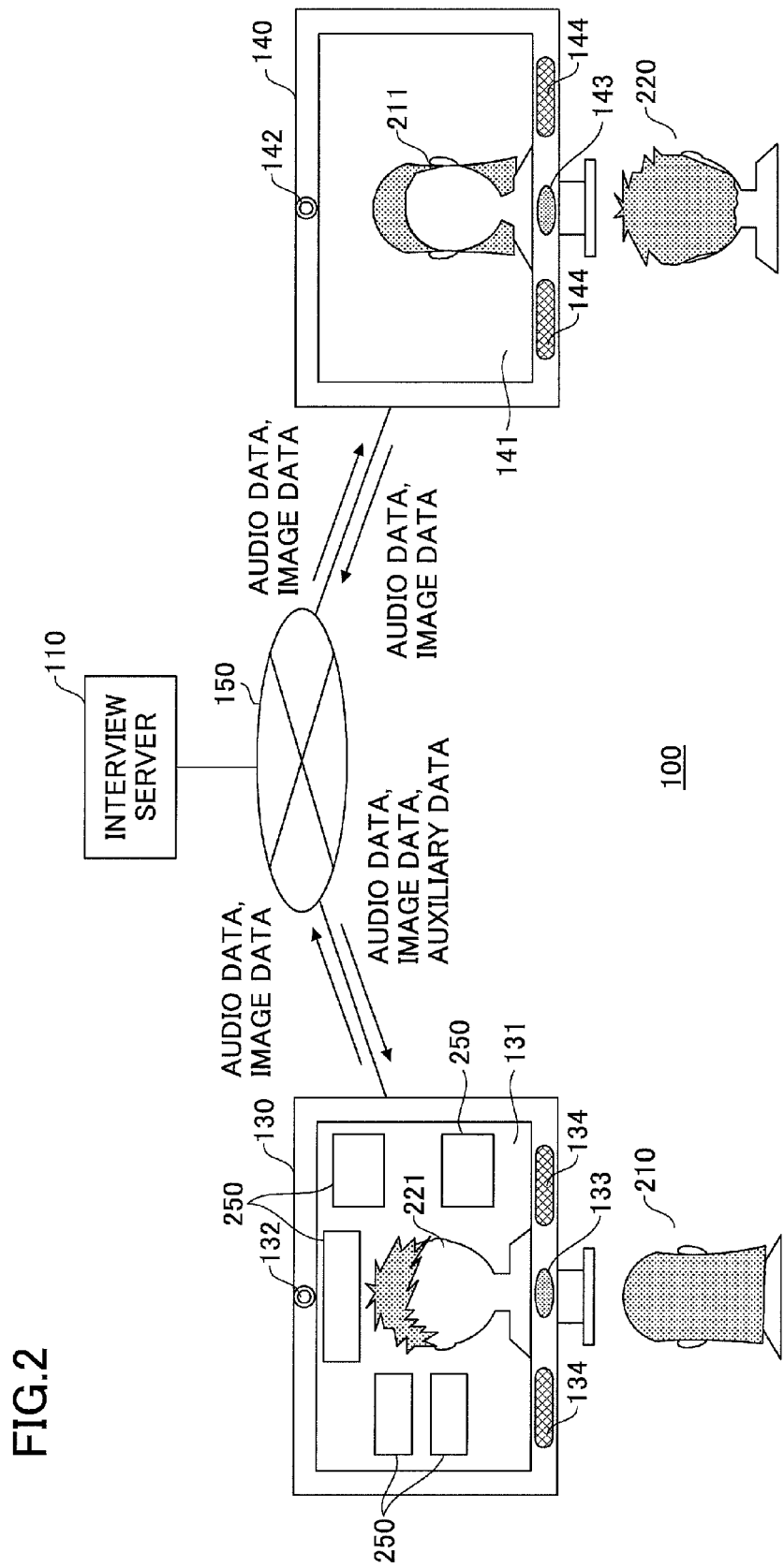
FIG. 2 is a diagram showing the use of a medical interview system and a flow of data.

In the following, an example of use of the medical interview system 100 and a flow of data are described. FIG. 2 is a diagram showing the use of the medical interview system 100 and a flow of data;

As mentioned above, in the vicinity of the display screen 131 of the information terminal 130, the imaging unit 132 that faces a display direction of the display screen 131 as a photographing direction thereof is disposed. In accordance with this, the imaging unit 132 can photograph a front image of a healthcare professional 210 seated in a location that faces the display screen 131.

As shown in FIG. 2, image data obtained by photographing using the imaging unit 132 is transmitted to the information terminal 140 via the network 150 and displayed in the display screen 141 of the information terminal 140.

Accordingly, a front image 211 of the healthcare professional 210 is displayed in the display screen 141 of the information terminal 140.

Further, in the vicinity of the display screen 131 of the information terminal 130, the loudspeaker unit 134 is disposed and outputs audio towards the healthcare professional 210. Further, in the vicinity of the display screen 131 of the information terminal 130, the microphone unit 133 is disposed and obtains voice uttered by the healthcare professional 210.

As shown in FIG. 2, audio data obtained by the microphone unit 133 is transmitted to the information terminal 140 via the network 150 and output from the loudspeaker unit 144 of the information terminal 140.

In the same manner, in the vicinity of the display screen 141 of the information terminal 140, the imaging unit 142 that faces a display direction of the display screen 141 as a photographing direction thereof is disposed. The imaging unit 142 photographs the front of an interviewee 220 seated in a location that faces the display screen 141.

As shown in FIG. 2, image data obtained by photographing using the imaging unit 142 is transmitted to the information terminal 130 via the network 150 and displayed in the display screen 131 of the information terminal 130. Accordingly, a front image 221 of the interviewee 220 is displayed in the display screen 131 of the information terminal 130.

Further, in the vicinity of the display screen 141 of the information terminal 140, the loudspeaker unit 144 is disposed and outputs audio towards the interviewee 220. Further, in the vicinity of the display screen 141 of the information terminal 140, the microphone unit 143 is disposed and obtains voice uttered by the interviewee 220.

As shown in FIG. 2, audio data obtained by the microphone unit 143 is transmitted to the information terminal 130 via the network 150 and output from the loudspeaker unit 134 of the information terminal 130.

Image data and audio data transmitted by the information terminal 140 are analyzed by the interview server 110 to create auxiliary data including information that indicates a current state of the interviewee and information that indicates a difference from a past state of the interviewee. The created auxiliary data is superimposed on image data to be transmitted to the information terminal information terminal 130. When the auxiliary data is superimposed on the image data, the interview server 110 arranges the auxiliary data such that the auxiliary data is classified and displayed in a plurality of fields 250 around a field where the front image 221 of the interviewee 220 is placed.

In accordance with this, in the display screen 131 of the information terminal 130, the auxiliary data including information that indicates the current state of the interviewee and information that indicates the difference from the past state of the interviewee is classified and displayed in the plurality of fields 250 around the field where the front image 221 of the interviewee 220 is placed.

In this manner, when the auxiliary data is displayed around the field where the front image 221 of the interviewee 220 is placed, the healthcare professional 210 can browse the auxiliary data while facing the display screen 131. In other words, it is not necessary for the healthcare professional 210 to face a direction different from the photographing direction and work in order to browse the auxiliary data. It is possible to prevent interruption of communication with the interviewee 220 in a virtual face-to-face state. As a result, the interviewee 220 will not experience alienation.

<3. Hardware Configuration of Interview Server>

Figure 3:
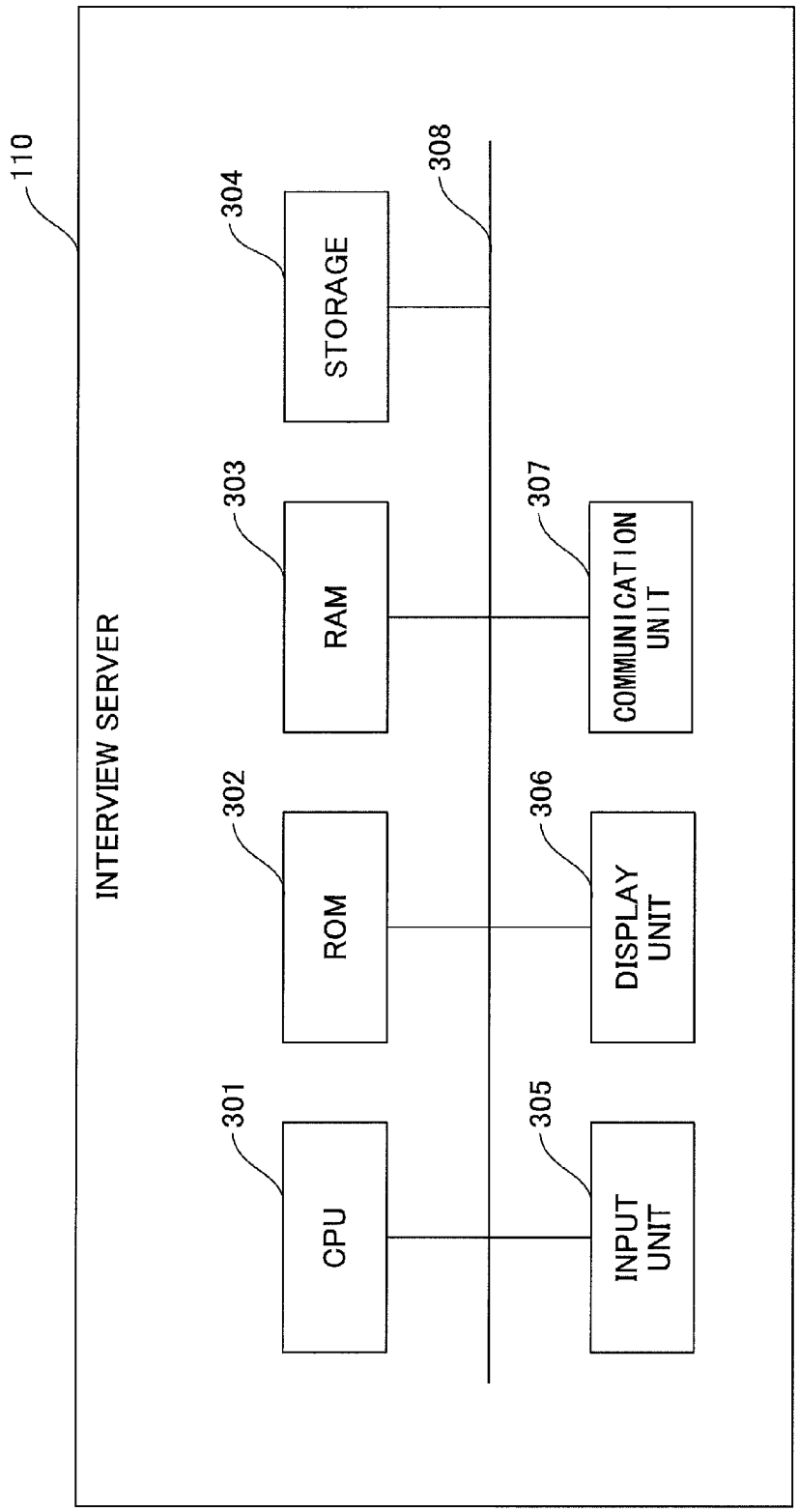
FIG. 3 is a diagram showing a hardware configuration of an interview server.

In the following, a hardware configuration of the interview server 110 is described. FIG. 3 is a diagram showing the hardware configuration of the interview server 110.

As shown in FIG. 3, the interview server 110 includes a Central Processing Unit (CPU) 301, a Read Only Memory (ROM) 302, a Random Access Memory (RAM) 303, and a storage 304. Further, the interview server 110 includes an input unit 305, a display unit 306, and a communication unit 307. All these units of the interview server 110 are interconnected via a bus 308.

CPU 301 is a computer that executes various types of programs (such as an interview program) stored in the storage 304.

The ROM 302 is a nonvolatile memory. The ROM 302 stores various types of programs, data, and the like necessary for the CPU 301 to execute the various types of programs stored in the storage 304. Specifically, the ROM 302 stores a boot program such as a Basic Input/Output System (BIOS) or an Extensible Firmware Interface (EFI).

The RAM 303 is a main memory device such as a Dynamic Random Access Memory (DRAM) or a Static Random Access Memory (SRAM). The RAM 303 functions as a work area where various types of programs stored in the storage 304 are loaded when the programs are executed by the CPU 301.

The storage 304 stores various types of programs to be executed by the CPU 301 and various types of DBs used when the various types of programs are executed by the CPU 301. Examples of the various types of DBs include the medical examination information DB 121, the working information DB 122, the question information DB 123, the advice information DB 124, the obtained information DB 125, and the graph information DB 126.

The input unit 305 is an interface for inputting various types of information to the interview server 110. The display unit 306 displays various types of information included in the interview server 110.

The communication unit 307 communicates with the information terminal 130 and the information terminal 140 via the network 150.

<4. Hardware Configuration of Information Terminal>

Figure 4:
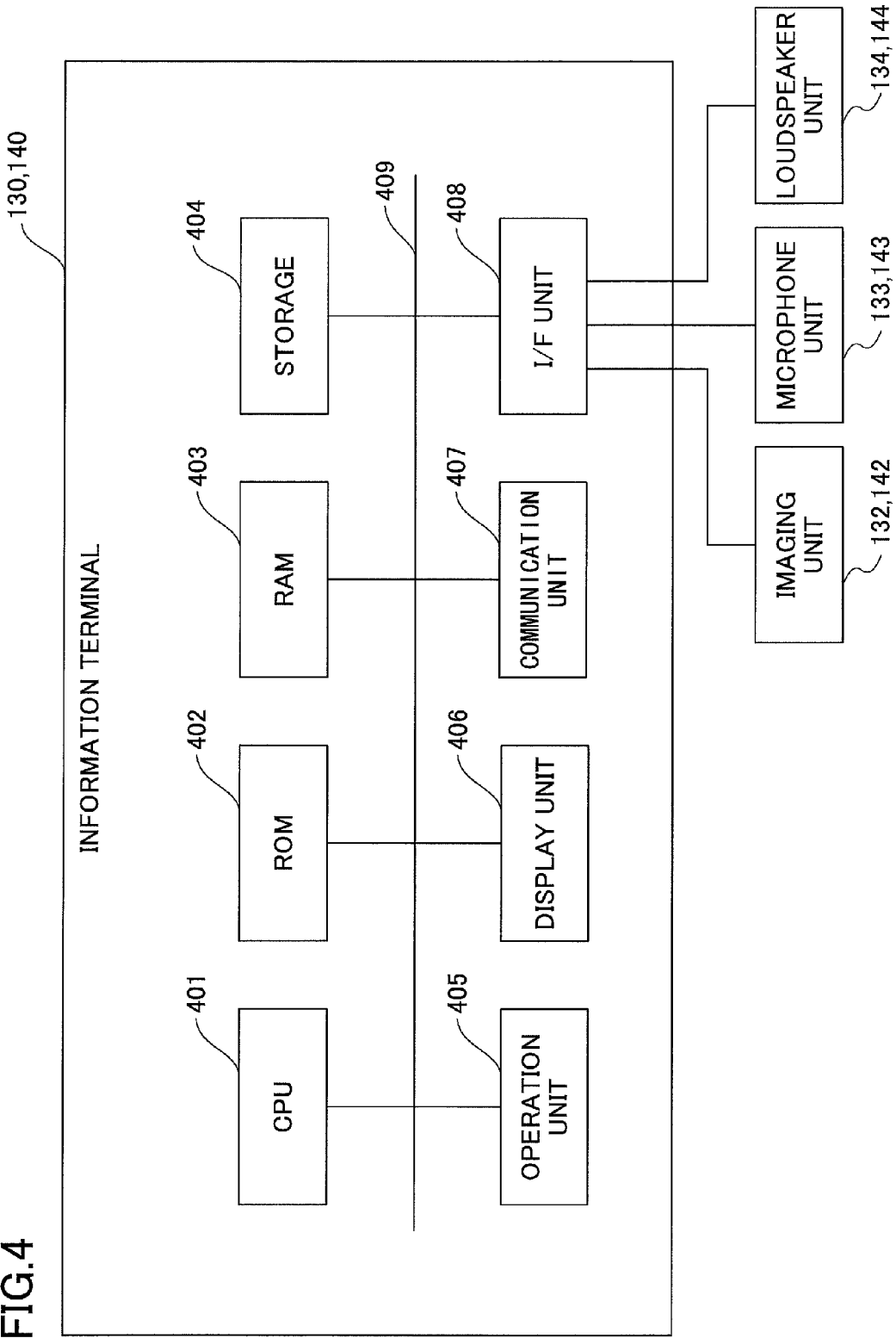
FIG. 4 is a diagram showing a hardware configuration of an information terminal.

In the following, a hardware configuration of the information terminal 130 and the information terminal 140 is described. FIG. 4 is a diagram showing the hardware configuration of the information terminal 130 and the information terminal 140.

As shown in FIG. 4, the information terminal 130 and the information terminal 140 include a CPU 401, a ROM 402, a RAM 403, and a storage 404. Further, the information terminal 130 and the information terminal 140 include an operation unit 405, a display unit 406, a communication unit 407, and an I/F unit 408. All these units of the information terminal 130 or the information terminal 140 are interconnected via a bus 409.

The CPU 401 is a computer that executes various types of programs stored in the storage 404.

The ROM 402 is a nonvolatile memory. The ROM 402 stores various types of programs, data, and the like necessary for the CPU 401 to execute the various types of programs stored in the storage 404. Specifically, the ROM 402 stores a boot program such as a Basic Input/Output System (BIOS) or an Extensible Firmware Interface (EFI).

The RAM 403 is a main memory device such as a Dynamic Random Access Memory (DRAM) or a Static Random Access Memory (SRAM). The RAM 403 functions as a work area where various types of programs stored in the storage 404 are loaded when the programs are executed by the CPU 401.

The storage 404 stores various types of programs to be executed by the CPU 401 and various types of information used when the various types of programs are executed by the CPU 401.

The operation unit 405 is used to input various types of instructions to the information terminal 130 and information terminal 140. The display unit 406 includes a display screen and displays image data received by the information terminal 130 or the information terminal 140. The communication unit 407 communicates with the medical interview system 100 via the network 150.

The I/F unit 408 is an interface for connecting to the imaging unit 132 (or the imaging unit 142), the microphone unit 133 (or the microphone unit 143), or the loudspeaker unit 134 (or the loudspeaker unit 144).

<5. Description of Various Types of Information>

In the following, various types of information stored in each DB included in the medical interview system 100 is described. From the various types of information described below, medical examination information, working information, obtained information, and graph information are used as information that indicates a past state of the interviewee 220 when deriving information that indicates a difference from the past state of the interviewee 220. In other words, the medical examination information DB 121, the working information DB 122, the obtained information DB 125, and the graph information DB 126 that store these types of information function as a storage unit that stores information to indicate the past state of the interviewee 220.

(1) Description of Medical Examination Information

In the following, medical examination information stored in the medical examination information DB 121 is described. FIG. 5 is a diagram showing a group of medical examination information sections. As shown in FIG. 5, the medical examination information DB 121 stores medical examination information about a plurality of interviewees. Since each set of medical examination information is in the same format, medical examination information 500 is described as an example.

The medical examination information 500 has a basic information section where attributes of an interviewee are written and a medical examination information section where a result of a medical examination of the interviewee is written.

As items of information, the basic information section includes "name," "age," "sex," "employee number," "year of entering company," and "department.". As items of information, the medical examination information section includes "height," "weight," "subjective symptom," "amount of tobacco," "amount of alcohol," "frequency of exercise," "meal condition," "name of disease, follow-up observation," "history of hospitalization," and "family medical history."

In each item of information in the medical examination information section, results of medical examinations of the interviewee for a plurality of years are written. Accordingly, the interview server 110 can calculate a difference value between a result of a past medical examination and a result of a current medical examination.

(2) Description of Working Information

In the following, working information stored in the working information DB 122 is described. FIG. 6 is a diagram showing a group of working information sections. As shown in FIG. 6, the working information DB 122 stores working information about a plurality of interviewees. Since each set of working information is in the same format, working information 600 is described as an example.

The working information 600 has a basic information section where attributes of an interviewee are written and a working information section of the interviewee. A description of the basic information section in the working information 600 is omitted because this basic information section is the same as the basic information section in the medical examination information 500.

In the working information section, a clock-in time and a clock-out time of the interviewee are written in association with each day of a month. The working information 600 has clock-in times and clock-out times written for the past one year in the working information section. However, a period of writing is not limited to one year.

(3) Description of Question Information

In the following, question information stored in the question information DB 123 is described. FIG. 7 is a diagram showing question information. As shown in FIG. 7, question information 700 includes "questions" and "display conditions" as items of information.

In the "questions," questions to ask the interviewee in order to more accurately comprehend a state of the interviewee are written. Each question is associated with conditions provided in the "display conditions."

In the "display conditions," conditions to automatically select each question written in the "questions" and display the selected question in the display screen 131 are provided. Items of the "display conditions" include "lack of sleep," "obesity," "increased stress," "increased drinking of alcohol," and "depressive tendency."

The interview server 110 determines which of the items "lack of sleep," "obesity," "increased stress," "increased drinking of alcohol," and "depressive tendency" applies by analyzing image data and audio data transmitted from the information terminal 140, the medical examination information 500, and the working information 600.

For example, if the interviewee 220 is determined as lacking sleep when the image data is analyzed, it is determined that a condition to display a question with an ID=2 is satisfied, so that the question with the ID=2 is automatically selected. In accordance with this, the question with the ID=2 is transmitted as auxiliary data to the information terminal 130 and is displayed in the display screen 131.

If the interviewee 220 is determined as obese when the medical examination information 500 is analyzed, it is determined that a condition to display a question with an ID=3 is satisfied, so that the question with the ID=3 is automatically selected. In accordance with this, the question with the ID=3 is transmitted as auxiliary data to the information terminal 130 and is displayed in the display screen 131.

Further, it is assumed that the interviewee 220 is determined as obese when the medical examination information 500 is analyzed, and the interviewee 220 is determined as having increased stress and a depressive tendency when the working information 600, image data, and audio data are analyzed. In this case, it is determined that a condition to display a question with an ID=4 is satisfied, so that the question with the ID=4 is automatically selected. In accordance with this, the question with the ID=4 is transmitted as auxiliary data to the information terminal 130 and is displayed in the display screen 131. In the same manner, if a condition provided in the "display conditions" is satisfied, a corresponding question is automatically selected.

(4) Description of Advice Information

In the following, advice information stored in the advice information DB 124 is described. FIG. 8 is a diagram showing advice information. As shown in FIG. 8, advice information 800 includes "advice" and "display conditions" as items of information.

In the "advice," pieces of advice to be given to the interviewee are written. Each piece of advice is associated with conditions provided in the "display conditions."

In the "display conditions," conditions to automatically select each piece of advice written in the "advice" and display the selected advice in the display screen 131 are provided. A description of items of the "display conditions" in the advice information 800 is omitted because the items are the same as the items of the "display conditions" in the question information 700.

In other words, the IDs in the advice information 800 correspond to the IDs in the question information 700. A question and a piece of advice to be selected if a display condition is satisfied are a question and a piece of advice having the same ID.

(5) Description of Obtained Information

In the following, first and second obtained information that is obtained based on image data and audio data transmitted by the information terminal 140 and is stored in the obtained information DB 125 is described. FIGS. 9A and 9B are diagrams showing the first and second obtained information.

FIG. 9A shows the first obtained information including image data and an analysis result of the image data. As shown in FIG. 9A, first obtained information 900 has a basic information section and an image information section for items of information. In addition, a description of the basic information section in the first obtained information 900 is omitted because this basic information section is the same as the basic information section in the medical examination information 500.

The image information section includes "pulse rate or heartbeat," "facial expression," "sentiment," "behavior," "appearance," and "image data" as items of information.

In the "pulse rate or heartbeat," a pulse rate per unit time calculated based on image data is recorded. Detection of beats based on the image data uses characteristics that hemoglobin in blood absorbs green light. Specifically, the beats are detected by calculating an average value of a brightness (RGB) value on a face surface from blood flow and constructing a pulse waveform from an amount of change of a calculated green component. In the "pulse rate or heartbeat," the pulse rate of the interviewee per unit time calculated based on detected beats is recorded.

In the "facial expression," a result of counting a number of facial expressions of the interviewee 220 classified into facial expression parameters in each predetermined period is recorded, the facial expressions being calculated based on an amount of characteristics extracted from a face field of the interviewee included in the image data. Facial expression parameters in the "facial expression" include "anger," "contempt," "dislike," "uneasiness," "joy," "sorrow," "surprise," and "neutrality."

In the "sentiment," an analysis result obtained by analyzing a color of a predetermined part of the face field of the interviewee included in the image data is recorded. Sentiment parameters in the "sentiment" include "color of face" and "color of lips".

In the "behavior," a calculation result obtained by calculating an amount of movement of each part of the interviewee included in the image data is recorded. Behavior parameters in the "behavior" include "head movement," "body movement," "lip movement," and "eye movement." For example, in the "head movement," an average value of movement of a head position of the interviewee in each predetermined period is recorded, the head position being detected from the image data and the average value being derived through calculation of the movement of the head position during a medical interview.

In the "appearance," an analysis result obtained by analyzing predetermined parts in fields other than the face field of the interviewee included in the image data is recorded. Appearance parameters in the "appearance" include "color of hair," "hairstyle," and "clothes." For example, in the "color of hair," color data obtained by analyzing a field of hair of the interviewee extracted from the image data is recorded. In the "hairstyle," an amount of characteristics that show a shape of hair of the interviewee is recorded, the amount of characteristics being obtained by analyzing a field of hair of the interviewee extracted from the image data. In the "clothes," an amount of characteristics that show untidiness of clothes of the interviewee is recorded, the amount of characteristics being obtained by analyzing a field of clothes of the interviewee extracted from the image data.

In the "image data," a storage location of the image data and a file name obtained during a medical interview are recorded.

In each item of information in the image information section, results of a plurality of past medical interviews are written. Accordingly, the interview server 110 can calculate a difference value between the results of the past medical interviews and a result of the medical interview currently being held.

FIG. 9B is a diagram showing the second obtained information including audio data and an analysis result of the audio data. As shown in FIG. 9B, second obtained information 910 has a basic information section and an audio information section for items of information. In addition, a description of the basic information section in the second obtained information 910 is omitted because this basic information section is the same as the basic information section in the medical examination information 500.

The audio information section includes "conversation" and "audio data" as items of information. In the "conversation," an analysis result of audio data obtained during the medical interview is recorded. Conversation parameters in the "conversation" include "tone," "number of speeches/speech period," "number of silences/silence period," and "negative expression."

In the "tone," an amount of characteristics obtained by making a language analysis of the audio data and calculating high and low patterns of sound used to distinguish meanings in the language is recorded.

In the "number of speeches/speech period," a number of speeches made by the interviewee or a period of time when the interviewee made speeches during the medical interview is calculated and recorded. In the "number of silences/silence period," a number of silences by the interviewee or a period of time when the interviewee is silent during the medical interview is calculated and recorded.

In the "negative expression," a number of negative expressions included in speeches of the interviewee is recorded, the number of negative expressions being calculated by performing the language analysis on the audio data. In the "audio data," a storage location of the audio data and a file name obtained during the medical interview are recorded.

In each item of information in the audio information section, results of a plurality of past medical interviews are written. Accordingly, the interview server 110 can calculate a difference value between the results of the past medical interviews and a result of the medical interview currently being held.

(6) Description of Graph Information

In the following, graph information stored in the graph information DB 126 is described. FIG. 10 is a diagram showing the graph information. As shown in FIG. 10, graph information 1000 has a basic information section and a graph information section for items of information. In addition, a description of the basic information section in the graph information 1000 is omitted because this basic information section is the same as the basic information section in the medical examination information 500.

The graph information section includes the following as items of information.

"Became less energetic"
"Became mentally unstable"
"Became less interested in appearances"
"Became taciturn suddenly"
"Made complaints"
"Lost (gained) weight suddenly"
"Increased amount of alcohol" and
"Increased number of late arrivals and absence"

In these items of information, a level value of each item is written, the level value being derived during the medical interview by analyzing the medical examination information 500, the working information 600, the first obtained information 900, and the second obtained information 910.

In each item of information in the graph information section, results of a plurality of past medical interviews are written. Accordingly, the interview server 110 can calculate a difference value between the results of the past medical interviews and a result of the medical interview currently being held.

<6. Functional Configuration of Interview Server>

Figure 11:
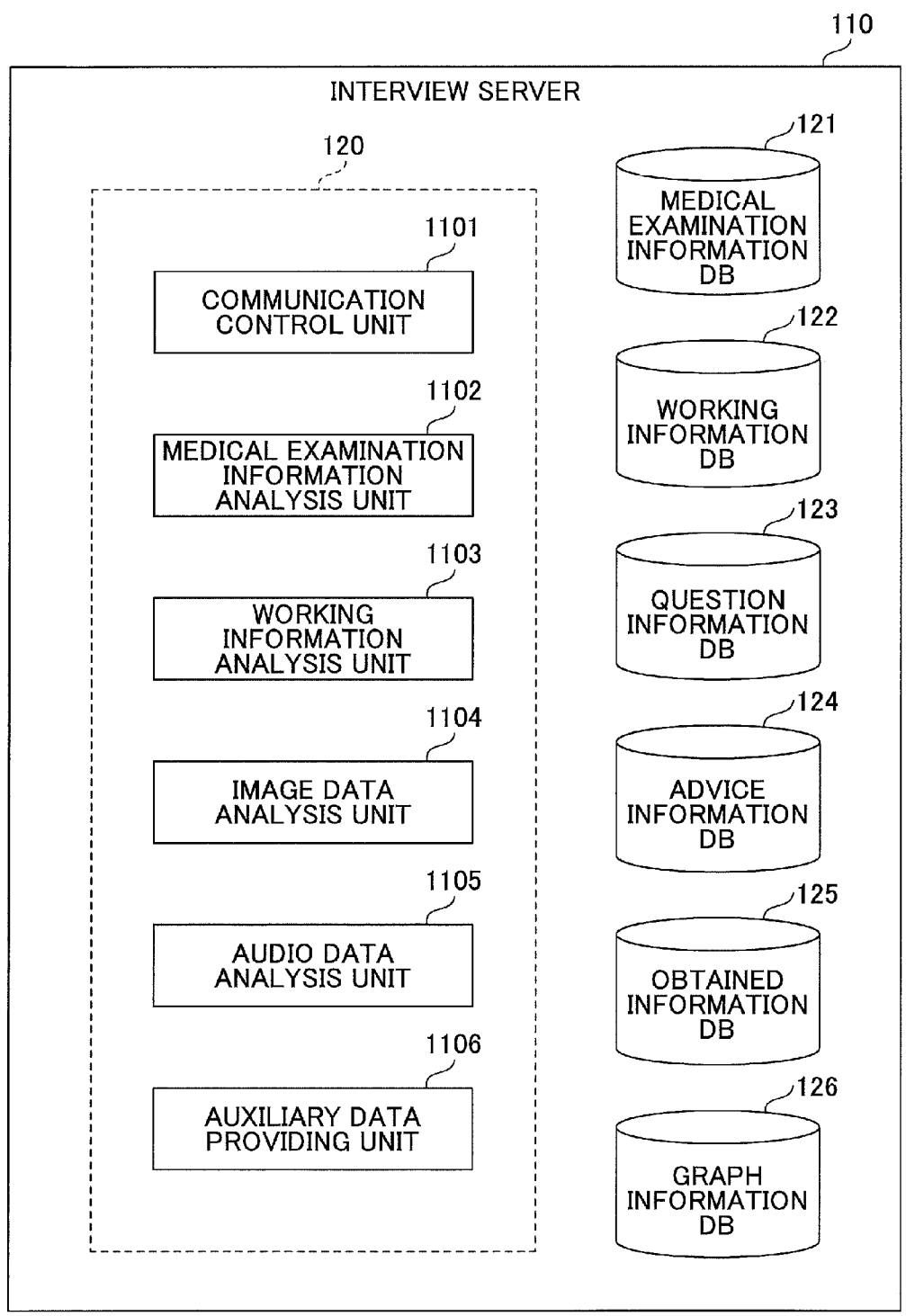
FIG. 11 is a diagram showing a functional configuration of an interview server.

In the following, functions implemented when the interview program 120 of the interview server 110 is executed by the CPU 301 are described. FIG. 11 is a diagram showing a functional configuration of the interview server 110.

As shown in FIG. 11, the functions implemented in the interview server 110 when the interview program 120 is executed by the CPU 301 include a communication control unit 1101, a medical examination information analysis unit 1102, a working information analysis unit 1103, an image data analysis unit 1104, an audio data analysis unit 1105, and an auxiliary data providing unit 1106.

The communication control unit 1101 controls communication between the information terminal 130 and the information terminal 140. Specifically, based on a connection request sent from the information terminal 130, the communication control unit 1101 sends an inquiry to the information terminal 140 and, if information (acceptance information) indicating acceptance is received from the information terminal 140, performs connection between the information terminal 130 and the information terminal 140. When the communication control unit 1101 performs the connection between the information terminal 130 and the information terminal 140, the communication control unit 1101 forwards image data and audio data transmitted by the information terminal 130 to the information terminal 140 and forwards image data and audio data transmitted by the information terminal 140 to the information terminal 130. In addition, when the communication control unit 1101 forwards the image data transmitted by the information terminal 140 to the information terminal 130, the communication control unit 1101 transmits image data on which auxiliary data provided by the auxiliary data providing unit 1106 is superimposed.

The medical examination information analysis unit 1102 extracts and analyzes the medical examination information 500 about the interviewee 220 from a group of medical examination information items stored in the medical examination information DB 121, so that the medical examination information analysis unit 1102 derives graph area display information, health information, and display condition information to be described below. Further, the medical examination information analysis unit 1102 reports the derived graph area display information, health information, and display condition information to the auxiliary data providing unit 1106.

The working information analysis unit 1103 extracts and analyzes the working information 600 about the interviewee 220 from a group of working information items stored in the working information DB 122, so that the working information analysis unit 1103 derives graph area display information and display condition information. Further the working information analysis unit 1103 reports the derived graph area display information and display condition information to the auxiliary data providing unit 1106.

The image data analysis unit 1104 analyzes image data received from the information terminal 140 and extracts facial expression parameters, sentiment parameters, behavior parameters, and appearance parameters. Further, based on each extracted parameter, the image data analysis unit 1104 derives graph area display information and display condition information and reports the information to the auxiliary data providing unit 1106. The image data analysis unit 1104 also analyzes the image data received from the information terminal 140 to calculate a pulse rate per unit time and reports the calculated pulse rate as mental information to the auxiliary data providing unit 1106. Further, the image data analysis unit 1104 derives display condition information based on a pulse waveform when the pulse rate is calculated and reports the derived display condition information to the auxiliary data providing unit 1106. Further, the image data analysis unit 1104 records the facial expression parameters, the sentiment parameters, the behavior parameters, the appearance parameters, and the pulse rate in the first obtained information 900 and stores the first obtained information 900 in the obtained information DB 125 when the medical interview ends.

The audio data analysis unit 1105 analyzes audio data received from the information terminal 140 and extracts conversation parameters. Further, based on the extracted conversation parameters, the audio data analysis unit 1105 derives graph area display information and display condition information and reports the information to the auxiliary data providing unit 1106. Further, the audio data analysis unit 1105 records the conversation parameters in the second obtained information 910 and stores the second obtained information 910 in the obtained information DB 125 when the medical interview ends.

The auxiliary data providing unit 1106 receives graph area display information, health information, mental information, and display condition information from the medical examination information analysis unit 1102, the working information analysis unit 1103, the image data analysis unit 1104, and the audio data analysis unit 1105.

The auxiliary data providing unit 1106 also generates, based on the received graph area display information, a graph image to be displayed in a graph field of the display screen 131. The auxiliary data providing unit 1106 also generates, based on the received health information, a health information field image to be displayed in a health information field of the display screen 131. The auxiliary data providing unit 1106 also generates, based on the received mental information, a mental information field image to be displayed in a mental information field of the display screen 131.

Further, the auxiliary data providing unit 1106 refers to the question information DB 123 to select a question that matches the received display condition information and generates a question field image to be displayed in a question field of the display screen 131. Further, the auxiliary data providing unit 1106 also refers to the advice information DB 124 to select a piece of advice that matches the received display condition information and generates an advice field image to be displayed in an advice field of the display screen 131.

Further, the auxiliary data providing unit 1106 outputs, as auxiliary data, the graph image, the health information field image, the question field image, and the advice field image that have been generated to the communication control unit 1101. The auxiliary data providing unit 1106 records each piece of the graph area display information used to generate the graph image in the graph information 1000 and stores the graph information 1000 in the graph information DB 126.

<7. Detailed Functions of Interview Server>

In the following, a process of each function of the interview server 110 is described in detail.

(1) Details of Medical Examination Information Analysis Unit

Figure 12:
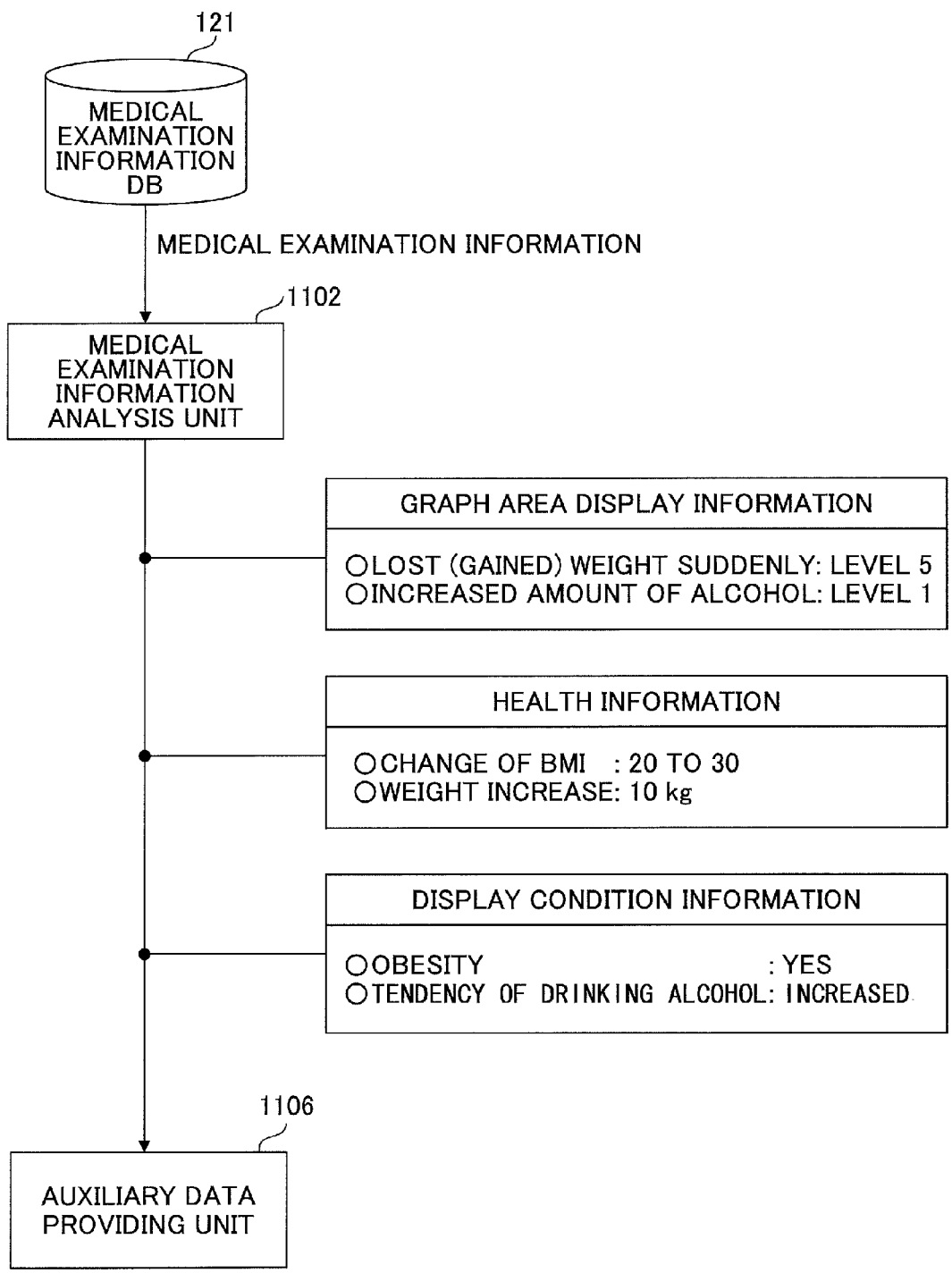
FIG. 12 is a diagram illustrating a process of a medical examination information analysis unit.

FIG. 12 is a diagram illustrating a process of the medical examination information analysis unit 1102. As shown in FIG. 12, the medical examination information analysis unit 1102 reads out the medical examination information 500 about the interviewee 220 from the medical examination information DB 121 and analyzes the read medical examination information 500. In accordance with this, the medical examination information analysis unit 1102 derives graph area display information, health information, and display condition information and reports the derived information to the auxiliary data providing unit 1106.

Specifically, if a difference between current weight of the interviewee 220 and corresponding weight in a previous year recorded in the "weight" of the medical examination information 500 is equal to or more than a predetermined threshold, the interviewee 220 is determined to have lost (gained) weight suddenly and a level of the item "Lost (gained) weight suddenly" is raised. By contrast, if the current weight is substantially the same as in the previous year, the level is lowered.

Further, if an amount of current alcohol consumed by the interviewee 220 recorded in the "amount of alcohol" of the medical examination information 500 has increased from an amount of alcohol in the previous year, the interviewee 220 is determined to have increased the amount of alcohol and a level of the item "Increased amount of alcohol" is raised. By contrast, if the amount of current alcohol is substantially the same as in the previous year, the level is lowered.

Further, the above-mentioned level value of the item "Lost (gained) weight suddenly" and the above-mentioned level value of the item "Increased amount of alcohol" are reported as graph area display information to the auxiliary data providing unit 1106. In other words, the graph area display information reported from the medical examination information analysis unit 1102 includes information that indicates a difference from a past state of the interviewee 220.

Further, a current Body Mass Index (BMI) value is calculated based on the current weight of the interviewee 220 recorded in the "weight" and a current height of the interviewee 220 recorded in the "height" of the medical examination information 500. Further, a BMI value in the previous year is calculated based on the weight and the height in the previous year. Further, a weight increase is calculated from a difference between the weight of the interviewee 220 in the previous year and the current weight recorded in the "weight" of the medical examination information 500.

Further, the BMI value in the previous year, the current BMI value, and the weight increase are reported as health information to the auxiliary data providing unit 1106. In other words, the health information reported from the medical examination information analysis unit 1102 includes information that indicates a difference from the past state of the interviewee 220.

Further, a health weight is calculated based on the weight of the interviewee 220 recorded in the "weight" and the height of the interviewee 220 recorded in the "height" of the medical examination information 500. Whether the interviewee 220 is obese is determined by referring to a list where a relationship between the health weight and a degree of obesity is defined in advance. Further, a change of the amount of alcohol consumed by the interviewee 220 in each year recorded in the "amount of alcohol" of the medical examination information 500 is calculated and it is determined that a tendency of drinking alcohol has increased if the change in each year has a positive value.

Further, a result of the determination of whether the interviewee 220 is obese and a result of the determination of whether the tendency of drinking alcohol has increased are reported as display condition information to the auxiliary data providing unit 1106. In other words, the display condition information reported from the medical examination information analysis unit 1102 includes information that indicates a current state of the interviewee 220 and information that indicates a difference from the past state of the interviewee 220.

(2) Details of Working Information Analysis Unit

Figure 13:
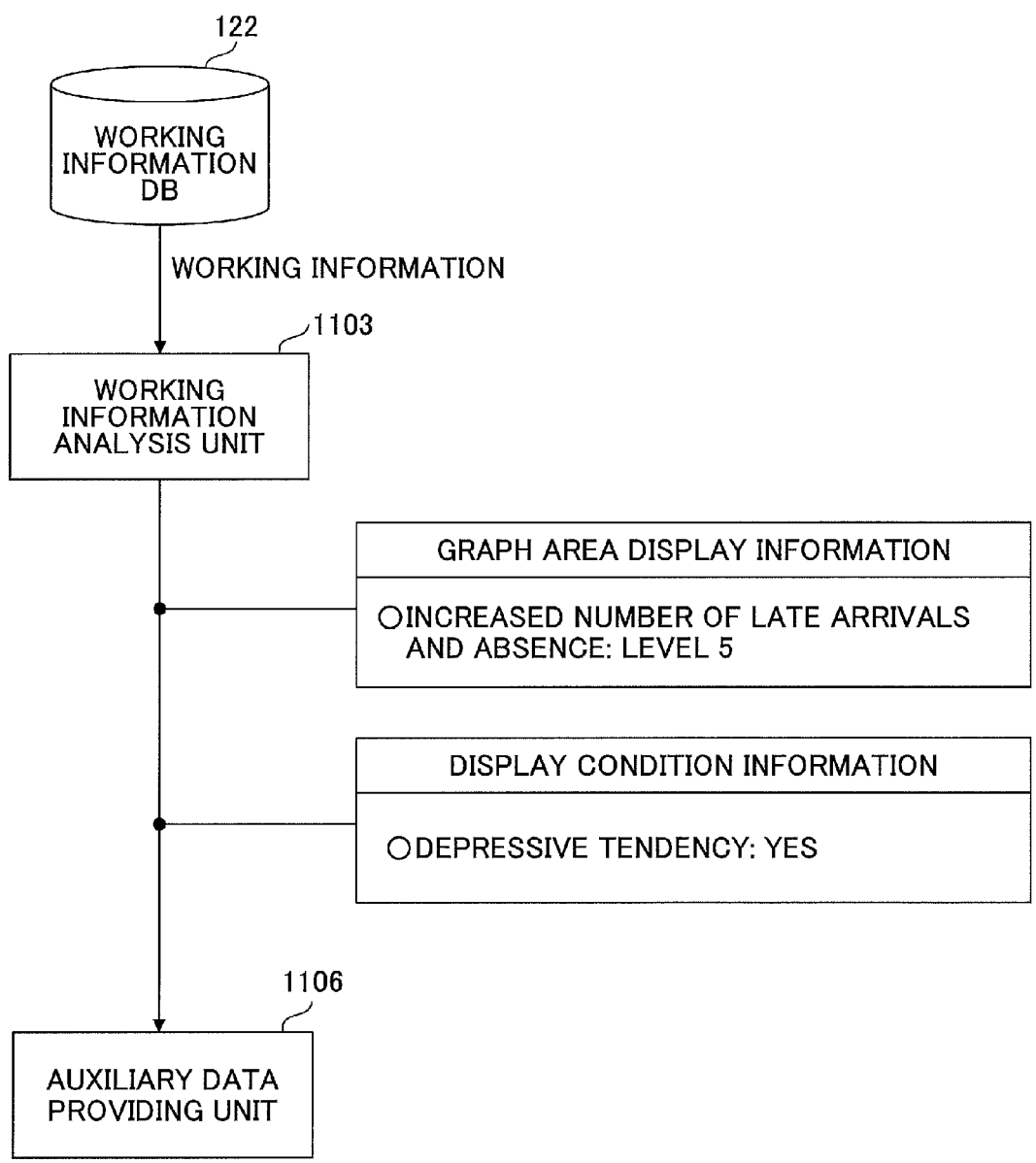
FIG. 13 is a diagram illustrating a process of a working information analysis unit.

FIG. 13 is a diagram illustrating a process of the working information analysis unit 1103. As shown in FIG. 13, the working information analysis unit 1103 reads out the working information 600 about the interviewee 220 from the working information DB 122 and analyzes the read working information 600. In accordance with this, the working information analysis unit 1103 derives graph area display information and display condition information and reports the derived information to the auxiliary data providing unit 1106.

Specifically, a number of late arrivals and absences in each predetermined period is calculated based on a clock-in time and a clock-out time recorded in the working information 600 and whether the number of late arrivals and absences has increased is determined. If the number of late arrivals and absences is determined to have increased, a level of the item "Increased number of late arrivals and absences" is raised. By contrast, if the number of late arrivals and absences is determined to have decreased, the level is lowered. Further, the above-mentioned level value of the item "Increased number of late arrivals and absences" is reported as graph area display information to the auxiliary data providing unit 1106. In other words, the graph area display information reported from the working information analysis unit 1103 includes information that indicates a difference from the past state of the interviewee 220.

Further, whether a day when the interviewee 220 was late based on a clock-in time recorded in the working information 600 follows a holiday is determined. If the day of late arrival follows the holiday, the interviewee 220 is determined to have a depressive tendency. Further, a result of the determination of whether the interviewee 220 has a depressive tendency is reported as display condition information to the auxiliary data providing unit 1106. In other words, the display condition information reported from the working information analysis unit 1103 includes information that indicates a difference from the past state of the interviewee 220.

(3) Details of Image Data Analysis Unit

Figure 14:
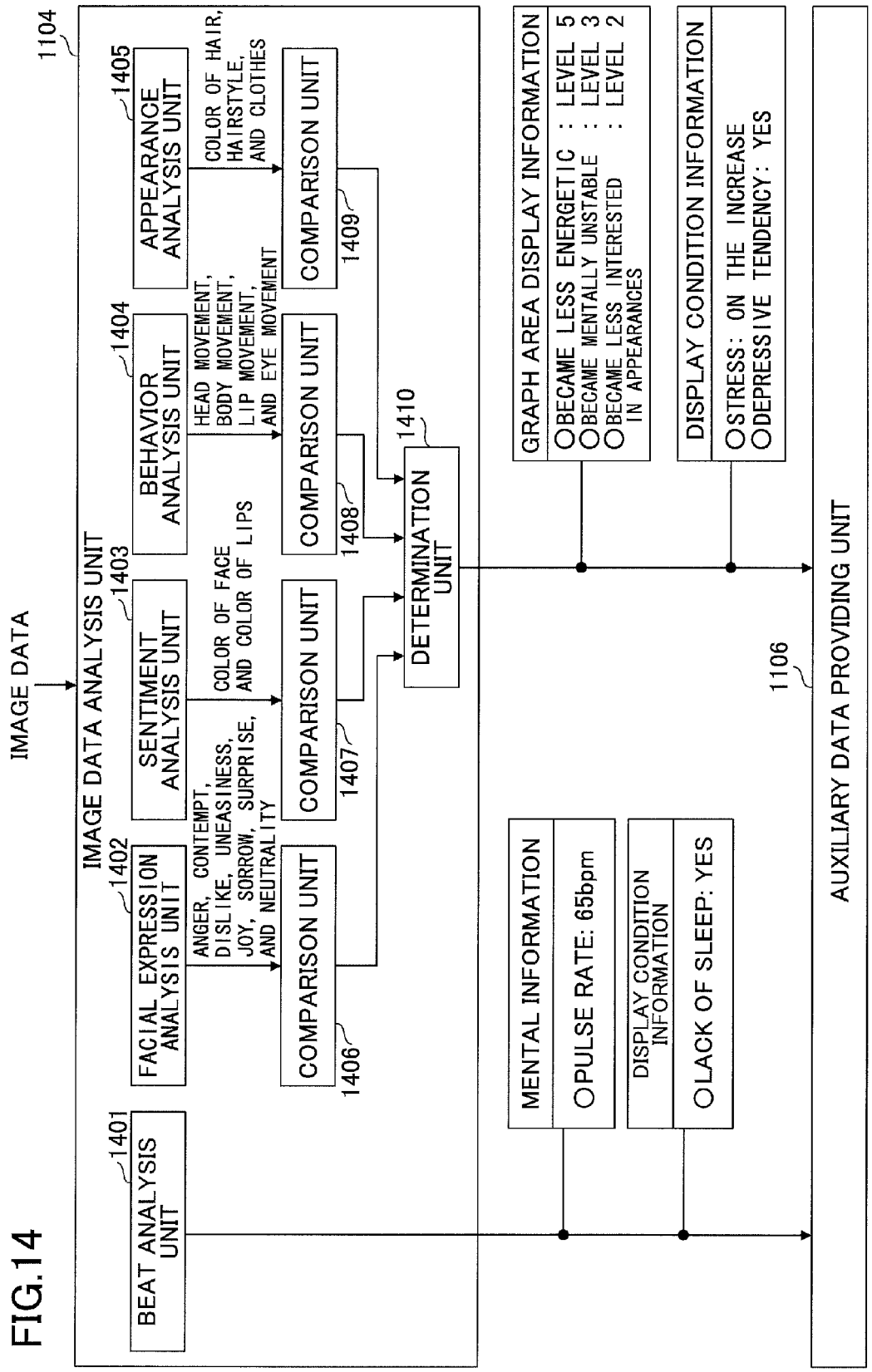
FIG. 14 is a diagram illustrating a process of an image data analysis unit.

FIG. 14 is a diagram illustrating a process of the image data analysis unit 1104. As shown in FIG. 14, the image data analysis unit 1104 includes a beat analysis unit 1401, a facial expression analysis unit 1402, a sentiment analysis unit 1403, a behavior analysis unit 1404, an appearance analysis unit 1405, comparison units 1406 to 1409, and a determination unit 1410.

The beat analysis unit 1401 detects a pulse waveform based on image data and calculates a pulse rate per unit time. Further, the beat analysis unit 1401 calculates a range of fluctuation of the detected pulse waveform and determines that the interviewee 220 is lacking sleep if the calculated range of fluctuation is narrower than a predetermined range of fluctuation. The calculated pulse rate is reported as mental information to the auxiliary data providing unit 1106 and a result of the determination of whether the interviewee 220 is lacking sleep is reported as display condition information to the auxiliary data providing unit 1106. In other words, the mental information and the display condition information reported from the image data analysis unit 1104 include information that indicates the current state of the interviewee 220.

The facial expression analysis unit 1402 determines a facial expression of the interviewee 220 based on an amount of characteristics extracted from the face field of the interviewee 220 included in the image data and outputs a result of counting a number of facial expressions classified into facial expression parameters in each predetermined period.

Figure 15:
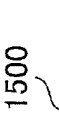
FIG. 15 is a diagram showing an analysis result by a facial expression analysis unit.

FIG. 15 is a diagram showing a result in which facial expressions of the interviewee 220 classified into facial expression parameters are counted per five minutes, the facial expressions of the interviewee 220 being classified based on image data on the interviewee 220 during a medical interview, and count values in each expression parameter are added when the medical interview ends. In FIG. 15, in a first period of five minutes, a number of facial expressions classified into the facial expression parameter=anger is 1, a number of facial expressions classified into the facial expression parameter=contempt is 2, and a number of facial expressions classified into the facial expression parameter=dislike is 10. Further, a number of facial expressions classified into the facial expression parameter=uneasiness is 8, a number of facial expressions classified into the facial expression parameter=joy is 0, a number of facial expressions classified into the facial expression parameter=sorrow is 1, and a number of facial expressions classified into the facial expression parameter=surprise is 0. In addition, a number of facial expressions not classified into any of these facial expression parameters (neutrality) is 16.

In this manner, by calculating a number of facial expressions classified into each facial expression parameter counted in the predetermined period (five minutes, for example), it is possible to estimate sentiment of the interviewee 220 in each time period during the medical interview.

Further, the facial expression analysis unit 1402 repeats the counting per five minutes until the medical interview ends. For example, the number of facial expressions classified into the facial expression parameter=anger is 1 in the first five minutes, the number is 2 from five to ten minutes, the number is 3 from ten to fifteen minutes, and the number is 0 thereafter until the medical interview ends.

In this manner, by continuously counting the number of facial expressions classified into each facial expression parameter based on a predetermined time unit during the medical interview, it is possible to estimate a change of sentiment of the interviewee 220 during the medical interview.

Further, the facial expression analysis unit 1402 sums up count values of each expression parameter when the medical interview ends. In FIG. 15, during the medical interview, a total number of facial expressions classified into the facial expression parameter=anger is 6, a total number of facial expressions classified into the facial expression parameter=contempt is 9, a total number of facial expressions classified into the facial expression parameter=dislike is 23, a total number of facial expressions classified into the facial expression parameter=uneasiness is 42. Further, a total number of facial expressions classified into the facial expression parameter=joy is 20, a total number of facial expressions classified into the facial expression parameter=sorrow is 12, a total number of facial expressions classified into the facial expression parameter=surprise is 24, and a total number of facial expressions classified into the facial expression parameter=neutrality is 90.

In this manner, by summing up count values of each expression parameter when the medical interview ends, it is possible to estimate general sentiment of the interviewee 220 through the medical interview.

Returning to FIG. 14, the comparison unit 1406 reads out a result of summing up in the facial expression parameters in a previous medical interview from the first obtained information 900, calculates an average value per five minutes, and compares the calculated average value with a count value of each facial expression parameter of the interviewee 220 per five minutes in the medical interview currently being held. If there is a facial expression parameter having a difference equal to or more than a predetermined threshold as a result of the comparison, the comparison unit 1406 reports the facial expression parameter to the determination unit 1410.

The sentiment analysis unit 1403 extracts the face field of the interviewee 220 from the image data and detects a color of the face and a color of the lips as sentiment parameters.

The comparison unit 1407 compares the sentiment parameters recorded when the previous medical interview was held from the first obtained information 900 with the sentiment parameters of the interviewee 220 in the medical interview currently being held. If there is a sentiment parameter having a difference equal to or more than a predetermined threshold as a result of the comparison, the comparison unit 1407 reports the sentiment parameter to the determination unit 1410.

The behavior analysis unit 1404 detects a head position, a body position, a lip position, and an iris position of the interviewee 220 from the image data and calculates an amount of movement of the detected head position, the detected body position, the detected lip position, and the detected iris position in each predetermined period.

The comparison unit 1408 reads out average values of the amounts of movements of the head position, the body position, the lip position, and the iris position in each predetermined period from the first obtained information 900, the positions being behavior parameters recorded when the previous medical interview was held. Then the comparison unit 1408 compares the read average values with the amounts of movements of the head position, the body position, the lip position, and the iris position of the interviewee 220 in each predetermined period in is a behavior parameter having a difference equal to or more than a predetermined threshold as a result of the comparison, the comparison unit 1408 reports the behavior parameter to the determination unit 1410.

The appearance analysis unit 1405 extracts the field of hair and the field of clothes of the interviewee 220 from the image data. As for the field of hair, the appearance analysis unit 1405 calculates a color of hair and an amount of characteristics that show a shape of the field of hair as appearance parameters. As for the field of clothes, the appearance analysis unit 1405 calculates an amount of characteristics that show untidiness of clothes as an appearance parameter.

The comparison unit 1409 compares the appearance parameters recorded when the previous medical interview was held from the first obtained information 900 with the appearance parameters of the interviewee 220 in the medical interview currently being held. If there is an appearance parameter having a difference equal to or more than a predetermined threshold as a result of the comparison, the comparison unit 1409 reports the appearance parameter to the determination unit 1410.

The determination unit 1410 outputs graph area display information and display condition information based on the reports from the comparison units 1406 to 1409.

For example, it is assumed that the comparison unit 1407 determines that there is a great difference between the color of the face of the interviewee 220 in the previous medical interview and the color of the face of the interviewee 220 in the medical interview currently being held. It is also assumed that the comparison unit 1406 determines that a change of facial expression of the interviewee 220 in the medical interview currently being held is smaller than a change of facial expression of the interviewee 220 in the previous medical interview. In this case, the determination unit 1410 determines that the interviewee 220 has become less energetic and raises a level of the item "Became less energetic" in the graph area display information. By contrast, if the difference of the color of the face of the interviewee 220 between the medical interviews is small and the change of facial expression is the same, the determination unit 1410 lowers the level of the item "Became less energetic."

Further, it is assumed that the comparison unit 1406 determines that a change of count values of the facial expression parameters of the interviewee 220 in each predetermined period of the medical interview currently being held has become greater in comparison with a change of count values of the facial expression parameters of the interviewee 220 in each predetermined period of the previous medical interview. In this case, the determination unit 1410 determines that a range of emotional ups and downs of the interviewee 220 has become greater. Further, it is assumed that the comparison unit 1406 determines that a result of summing up of count values in the facial expression parameters of the interviewee 220 in the medical interview currently being held has become greater in comparison with a result of summing up of count values in the facial expression parameters of the interviewee 220 in the previous medical interview. In this case, the determination unit 1410 determines that the interviewee 220 has expressed feelings more in comparison with the previous medical interview. In this manner, if the range of emotional ups and downs has become greater and more facial expressions are made, the determination unit 1410 raises a level of the item "Became mentally unstable" in the graph area display information. By contrast, if the range of emotional ups and downs of the interviewee 220 remains unchanged and a number of facial expressions that have been made remains unchanged, the determination unit 1410 lowers the level of the item "Became mentally unstable."

Further, it is assumed that the comparison unit 1409 determines that the hair of the interviewee 220 has become untidy in comparison with the previous medical interview based on the amount of characteristics that show the shape of the field of hair and it is also assumed that the comparison unit 1409 determines that clothes have become darker in comparison with the previous medical interview based on a color of the field of clothes. Further, it is also assumed that the comparison unit 1409 determines that the clothes of the interviewee 220 have become untidy in comparison with the previous medical interview based on the amount of characteristics that show untidiness of the clothes in the field of clothes. In this case, the determination unit 1410 determines that the interviewee 220 has become less interested in appearances and raises a level of the item "Became less interested in appearances" in the graph area display information. By contrast, if there is no untidy hair or clothes in comparison with the previous medical interview and the color of the clothes remains unchanged, the determination unit 1410 lowers the level of the item "Became less interested in appearances."

Further, the determination unit 1410 reports the above-mentioned level value of the item "Became less energetic," the above-mentioned level value of the item "Became mentally unstable," and the above-mentioned level value of the item "Became less interested in appearances" as graph area display information to the auxiliary data providing unit 1106. In other words, the graph area display information reported from the image data analysis unit 1104 includes information that indicates a difference from the past state of the interviewee 220.

Further, in the graph area display information, if the level of the item "Became less energetic" is raised and the level of the item "Became less interested in appearances" is raised, the determination unit 1410 determines that the "stress" is on the increase, the "stress" being one of the items of the display condition information. By contrast, if the level of the item "Became less energetic" is lowered and the level of the item "Became less interested in appearances" is lowered, the determination unit 1410 determines that the "stress" is on the decrease, the "stress" being one of the items of the display condition information.

Further, in the graph area display information, if the level of the item "Became mentally unstable" is raised, the determination unit 1410 determines that the "depressive tendency" shows "Yes," the "depressive tendency" being one of the items of the display condition information. By contrast, if the level of the item "Became mentally unstable" is lowered, the determination unit 1410 determines that the "depressive tendency" shows "No," the "depressive tendency" being one of the items of the display condition information.

Further, the determination unit 1410 reports a result of the determination of the stress and a result of the determination of the presence or absence of the depressive tendency as display condition information to the auxiliary data providing unit 1106. In other words, the display condition information reported from the image data analysis unit 1104 includes information that indicates a difference from the past state of the interviewee 220.

(4) Details of Audio Data Analysis Unit

FIG. 16 is a diagram illustrating a process of the audio data analysis unit 1105. As shown in FIG. 16, the audio data analysis unit 1105 includes a time analysis unit 1601, a conversation analysis unit 1602, a tone analysis unit 1603, comparison units 1604 to 1606, and a determination unit 1607.

The time analysis unit 1601 calculates a speech period and a silence period of the interviewee 220 based on audio data. FIGS. 17A to 17C are diagrams schematically showing the speech period and the silence period of the interviewee 220 and a speech period and a silence period of the healthcare professional 210 during a medical interview.

FIG. 17A schematically shows the speech period and the silence period of interviewee 220 and the speech period and the silence period of healthcare professional 210 in the previous medical interview. In FIG. 17A, an abscissa indicates time elapsed in the medical interview, an upper stage includes speech periods (blank parts) and silence periods (shaded parts) of the interviewee 220, and a lower stage includes speech periods (blank parts) and silence periods (shaded parts) of the healthcare professional 210.

FIG. 17B schematically shows the speech period and the silence period of interviewee 220 and the speech period and the silence period of healthcare professional 210 in the medical interview currently being held. In FIG. 17B, an abscissa indicates time elapsed in the medical interview, an upper stage includes speech periods (blank parts) and silence periods (shaded parts) of the interviewee 220, and a lower stage includes speech periods (blank parts) and silence periods (shaded parts) of the healthcare professional 210.

The time analysis unit 1601 calculates a total length of the speech periods of the interviewee 220 by summing up lengths of the speech periods (blank parts) of the interviewee 220. The time analysis unit 1601 calculates a total length of the silence periods of the interviewee 220 by summing up lengths of the silence periods (shaded parts) of the interviewee 220.

The comparison unit 1604 calculates a difference between the total length of the speech periods of the interviewee 220 during the medical interview calculated by the time analysis unit 1601 and the total length of the speech periods of the interviewee 220 in the previous medical interview recorded in the second obtained information 910. The comparison unit 1604 also calculates a difference between the total length of the silence periods of the interviewee 220 during the medical interview calculated by the time analysis unit 1601 and the total length of the silence periods of the interviewee 220 in the previous medical interview recorded in the second obtained information 910. If the calculated difference is equal to or more than a predetermined threshold, the comparison unit 1604 reports this fact to the determination unit 1607.

FIG. 17C is a diagram showing the calculated difference. The diagram shown in FIG. 17C includes a result of the calculation of the difference between the total length of the speech periods of the interviewee 220 during the medical interview currently being held and the total length of the speech periods of the interviewee 220 in the previous medical interview. The diagram shown in FIG. 17C also includes a result of the calculation of the difference between the total length of the silence periods of the interviewee 220 during the medical interview currently being held and the total length of the silence periods of the interviewee 220 in the previous medical interview. The comparison unit 1604 determines whether the difference shown in FIG. 17C is equal to or more than a predetermined threshold and reports a result of the determination to the determination unit 1607.

The conversation analysis unit 1602 extracts negative expressions used by the interviewee 220 from conversations included in audio data by performing a speech recognition process on the audio data and making a language analysis. The conversation analysis unit 1602 counts a number of the extracted negative expressions.

The comparison unit 1605 reads out a number of negative expressions used by the interviewee 220 in the previous medical interview from the second obtained information 910. Further, the comparison unit 1605 compares the number of the negative expressions counted in the conversation analysis unit 1602 with the number of negative expressions used by the interviewee 220 in the previous medical interview read from the second obtained information 910. If a difference obtained as a result of the comparison is equal to or more than a predetermined threshold, the comparison unit 1605 reports this fact to the determination unit 1607.

The tone analysis unit 1603 calculates an amount of characteristics (amount of tone characteristics) of high and low patterns of sound used to distinguish meanings in the language by performing a speech recognition process on the audio data and making a language analysis. The comparison unit 1606 compares the amount of tone characteristics calculated by the tone analysis unit 1603 with an amount of tone characteristics calculated from audio data in the previous medical interview read from the second obtained information 910. If a difference obtained as a result of the comparison is equal to or more than a predetermined threshold, the comparison unit 1606 reports this fact to the determination unit 1607.

The determination unit 1607 outputs graph area display information and display condition information based on the reports from the comparison units 1604 to 1606.

For example, it is assumed that the comparison unit 1604 determines that there is a great difference between the total length of the silence periods of the interviewee 220 in the previous medical interview and the total length of the silence periods of the interviewee 220 in the medical interview currently being held. In this case, the determination unit 1607 determines that the interviewee 220 has become taciturn suddenly and raises a level of the item "Became taciturn suddenly" in the graph area display information. By contrast, if the difference between the total lengths of the silence periods of the interviewee 220 is small, the determination unit 1607 lowers the level of the item "Became taciturn suddenly."

Further, it is assumed that the comparison unit 1605 determines that there is a great difference between the number of negative expressions used by the interviewee 220 in conversations in the previous medical interview and the number of negative expressions used by the interviewee 220 in conversations in the medical interview currently being held. Further, it is assumed that the comparison unit 1606 determines that there is a great difference between the amount of tone characteristics of the interviewee 220 in conversations in the previous medical interview and the amount of tone characteristics of the interviewee 220 in conversations in the medical interview currently being held and also determines that the tone of the interviewee 220 has become lower in the conversations in the medical interview currently being held. In this case, the determination unit 1607 determines that the interviewee 220 has made complaints and raises a level of the item "Made complaints" in the graph area display information. By contrast, if it is determined the number of negative expressions used by the interviewee 220 is reduced and the tone has become higher, the determination unit 1607 lowers the level of the item "Made complaints" in the graph area display information.

Further, the determination unit 1607 reports the above-mentioned level value of the item "Became taciturn suddenly" and the above-mentioned level value of the item "Made complaints" as graph area display information to the auxiliary data providing unit 1106. In other words, the graph area display information reported from the audio data analysis unit 1105 includes information that indicates a difference from the past state of the interviewee 220.

Further, in the graph area display information, if the level of the item "Became taciturn suddenly" is raised, the determination unit 1607 determines that the "stress" is on the increase, the "stress" being one of the items of the display condition information. By contrast, if the level of the item "Became taciturn suddenly" is lowered, the determination unit 1607 determines that the "stress" is on the decrease, the "stress" being one of the items of the display condition information.

Further, in the graph area display information, if the level of the item "Made complaints" is raised, the determination unit 1607 determines that the "depressive tendency" shows "Yes," the "depressive tendency" being one of the items of the display condition information. By contrast, if the level of the item "Made complaints" is lowered, the determination unit 1607 determines that the "depressive tendency" shows "No," the "depressive tendency" being one of the items of the display condition information.

Further, the determination unit 1607 reports a result of the determination of the stress and a result of the determination of the presence or absence of the depressive tendency as display condition information to the auxiliary data providing unit 1106. In other words, the display condition information reported from the audio data analysis unit 1105 includes information that indicates a difference from the past state of the interviewee 220.

(5) Details of the Auxiliary Data Providing Unit

Figure 18:
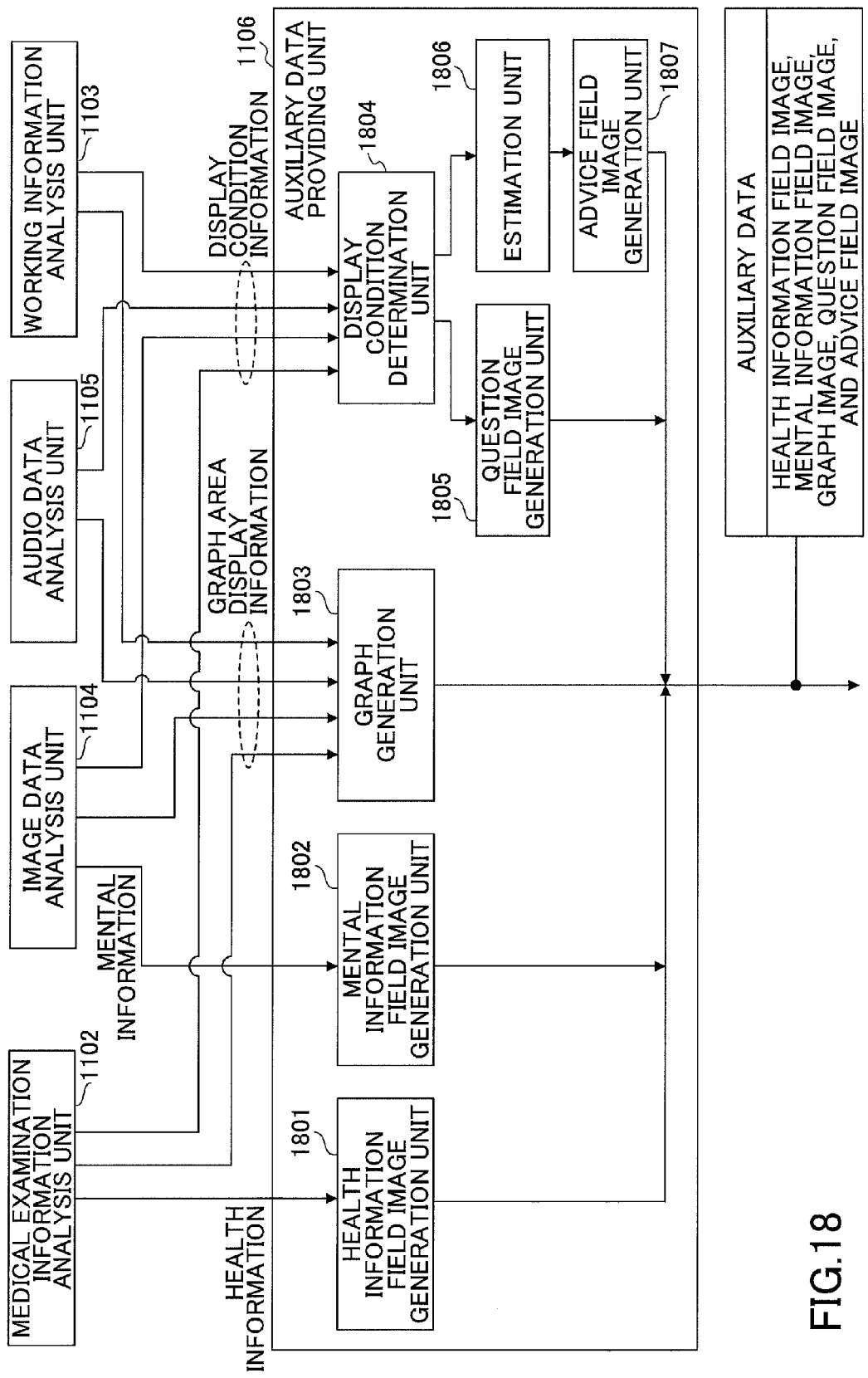
FIG. 18 is a diagram illustrating a process of an auxiliary data providing unit.

FIG. 18 is a diagram illustrating a process of the auxiliary data providing unit 1106. As shown in FIG. 18, the auxiliary data providing unit 1106 includes a health information field image generation unit 1801, a mental information field image generation unit 1802, a graph generation unit 1803, a display condition determination unit 1804, a question field image generation unit 1805, an estimation unit 1806, and an advice field image generation unit 1807.

The health information field image generation unit 1801 generates a health information field image based on health information reported from the medical examination information analysis unit 1102. In addition, the health information reported from the medical examination information analysis unit 1102 includes a change of BMI and a weight increase.

The mental information field image generation unit 1802 generates a mental information field image based on mental information reported from the image data analysis unit 1104. In addition, the mental information reported from the image data analysis unit 1104 includes a pulse rate per unit time.

The graph generation unit 1803 generates a graph based on graph area display information reported from the medical examination information analysis unit 1102, the working information analysis unit 1103, the image data analysis unit 1104, and the audio data analysis unit 1105. The working information analysis unit 1103 receives a level value of the item "Lost (gained) weight suddenly" and a level value of the item "Increased amount of alcohol" from the medical examination information analysis unit 1102. The working information analysis unit 1103 receives a level value of the item "Became less energetic", a level value of the item "Became mentally unstable", and a level value of the item "Became less interested in appearances" from the image data analysis unit 1104. The graph generation unit 1803 receives a level value of the item "Became taciturn suddenly" and a level value of the item "Made complaints" from the audio data analysis unit 1105. And the graph generation unit 1803 receives a level value of the item "Increased number of late arrivals and absence" from the working information analysis unit 1103.

The graph generation unit 1803 generates a graph by plotting the level value of each item received and outputs a graph image.

The display condition determination unit 1804 receives display condition information reported from the medical examination information analysis unit 1102, the working information analysis unit 1103, the image data analysis unit 1104, and the audio data analysis unit 1105. The display condition determination unit 1804 also reads out the question information 700 and determines which display condition provided in the question information 700 is included in the sets of received display condition information. Further, the display condition determination unit 1804 selects a question that matches the provided display condition.

The question field image generation unit 1805 generates a question field image based on the question selected in the display condition determination unit 1804.

The display condition determination unit 1804 reads out the advice information 800 and determines which display condition provided in the advice information 800 is included in the received display condition information. Further, the display condition determination unit 1804 selects a piece of advice that matches the provided display condition.

The estimation unit 1806 extracts an estimated value depending on the piece of advice selected in the display condition determination unit 1804. For example, it is assumed that the display condition determination unit 1804 determines that the display condition of obesity is included in the display condition information and the display condition determination unit 1804 selects a piece of advice "Take a balanced diet while quitting between meals."

In this case, the estimation unit 1806 calculates a past BMI value based on the medical examination information 500 and estimates an increase of the BMI value in the future. Further, the estimation unit 1806 extracts a relationship between the BMI value and a risk of developing diabetes from predetermined statistical information and calculates a risk of developing diabetes based on the estimated increase.

Further, it is assumed that the display condition determination unit 1804 determines that the display condition of increased drinking of alcohol is included in the display condition information and the display condition determination unit 1804 selects a piece of advice "Exercise at least once a week."

In this case, the estimation unit 1806 calculates an amount of past alcohol based on the medical examination information 500 and estimates an increase of an amount of alcohol in the future. Further, the estimation unit 1806 extracts a relationship between the amount of alcohol and a risk of developing liver cancer from predetermined statistical information and calculates a risk of developing liver cancer based on the estimated increase.

The advice field image generation unit 1807 generates an advice field image using the piece of advice selected by the display condition determination unit 1804 and the risk of development calculated by the estimation unit 1806.

The auxiliary data providing unit 1106 reports the health information field image, the mental information field image, the graph image, the question field image, and the advice field image as auxiliary data to the communication control unit 1101.

<8. Description of Display Screen>

Figure 19:
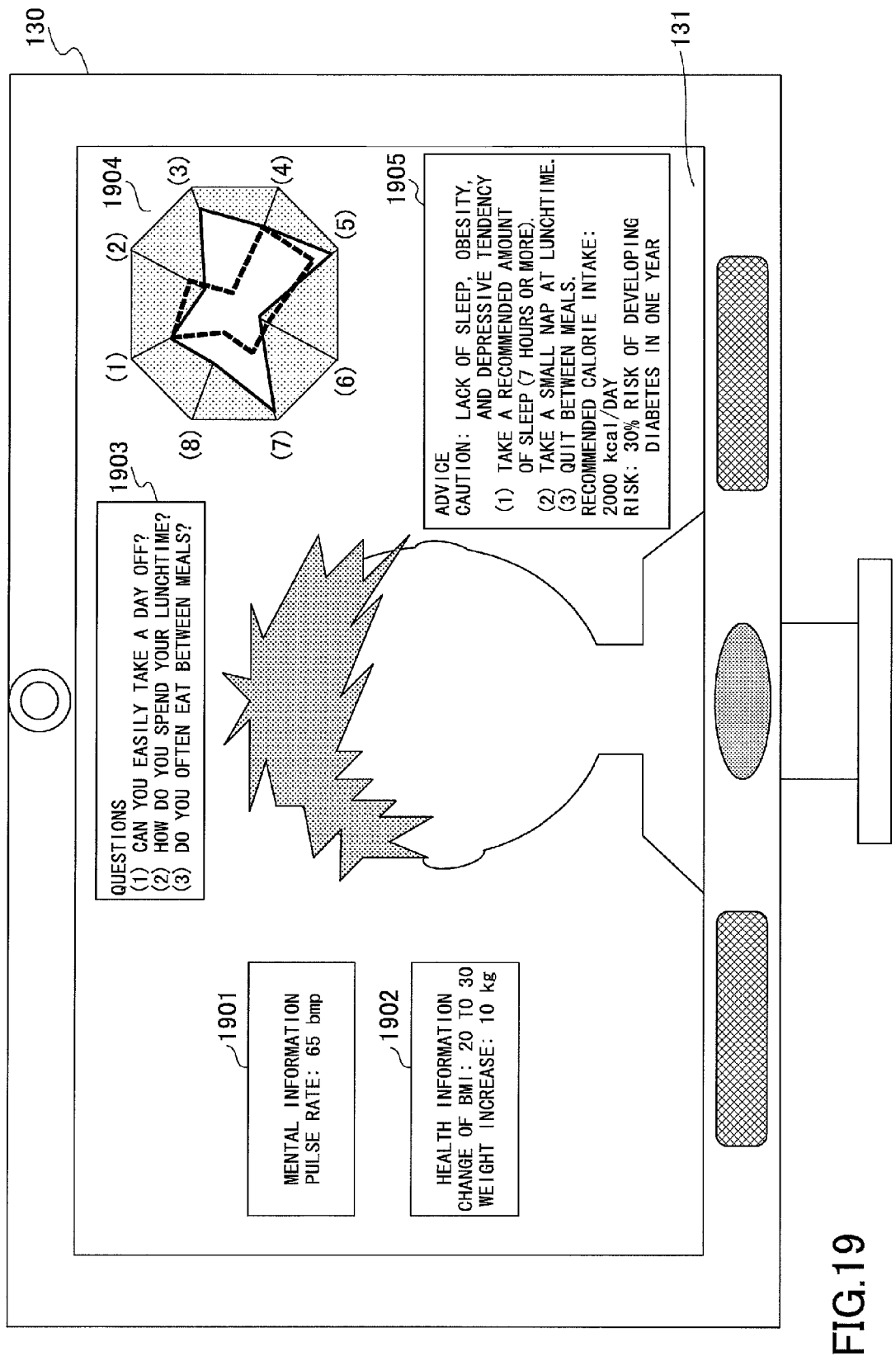
FIG. 19 is a diagram showing a display screen rendered in an information terminal used by a healthcare professional.

In the following, the display screen 131 to be rendered in the information terminal 130 used by the healthcare professional 210 is described. FIG. 19 is a diagram showing the display screen 131 rendered in the information terminal 130 used by the healthcare professional 210.

As shown in FIG. 19, the display screen 131 rendered in the information terminal 130 used by the healthcare professional 210 includes a mental information field 1901, a health information field 1902, a question field 1903, a graph field 1904, and an advice field 1905.

In the mental information field 1901, a mental information field image generated by the mental information field image generation unit 1802 is displayed. In FIG. 19, the mental information field image includes a pulse rate per minute=65 bpm.

In the health information field 1902, a health information field image generated by the health information field image generation unit 1801 is displayed. In FIG. 19, the health information field image indicates that a BMI value of the interviewee 220 has increased from 22 to 30 and weight of the interviewee 220 has increased by 10 Kg.

In the question field 1903, a question field image generated by the question field image generation unit 1805 is displayed. In FIG. 19, questions "Can you easily take a day off?," "How do you spend your lunchtime?," and "Do you often each between meals?" are selected in response to determination that display conditions of lack of sleep, obesity, and depressive tendency are included in the display condition information. Accordingly, the question field image includes these questions.

In the graph field 1904, a graph image generated by the graph generation unit 1803 is displayed. As shown in FIG. 19, in the graph field 1904, a graph image (dashed line) generated in the previous medical interview and a graph image (solid line) generated in the medical interview currently being held are displayed together. In accordance with this, it is possible to easily compare the graph image of the current medical interview with the graph image of the previous medical interview. Further, an item with a substantial change from the previous medical interview may be displayed differently from the other items so that the healthcare professional 210 will surely recognize the item with a substantial change without overlooking it.

In FIG. 19, the level value of item (1) "Became less energetic" remains 2.5 in the previous medical interview and in the current medical interview. While the level value of item (2) "Became mentally unstable" is 2 in the previous medical interview, the level value is 1 in the current medical interview. Further, while the level value of the item (3) "Became less interested in appearances" is 1 in the previous medical interview, the level value increases to 4 in the current medical interview. Further, the level value of item (4) "Became taciturn suddenly" remains 2.5 in the previous medical interview and in the current medical interview. Further, while the level value of item (5) "Made complaints" is 4 in the previous medical interview, the level value increases to 5 in the current medical interview. Further, the level value of item (6) "Lost (gained) weight suddenly" remains 1 in the previous medical interview and in the current medical examination. Further, while the level value of item (7) "Increased amount of alcohol" is 1 in the previous medical interview, the level value increases to 5 in the current medical interview. Further, while the level value of item (8) "Increased number of late arrivals and absence" is 1 in the previous medical interview, the level value increases to 2.5 in the current medical interview.

In the advice field 1905, an advice field image generated by the advice field image generation unit 1807 is displayed. In FIG. 19, since it is determined that display conditions of lack of sleep, obesity, and depressive tendency are included in the display condition information, the advice field image includes the lack of sleep, the obesity, and the depressive tendency as cautions. Further, since it is determined that the display conditions of lack of sleep, obesity, and depressive tendency are included in the display condition information, the advice field image shows pieces of advice "Take a recommended amount of sleep (7 hours or more)," "Take a small nap at lunchtime," and "Quit between meals."

Further, since the estimation unit 1806 obtains "recommended calorie intake: 2000 kcal/day" as statistical information in response to the determination that the display condition of obesity is included, the advice field image shows the statistical information. Further, since the estimation unit 1806 calculates the risk of developing diabetes in response to the determination that the display condition of obesity is included, the advice field image shows the risk of development.

<9. Flow of Medical Interview Process in Medical Interview System>

Figure 20:
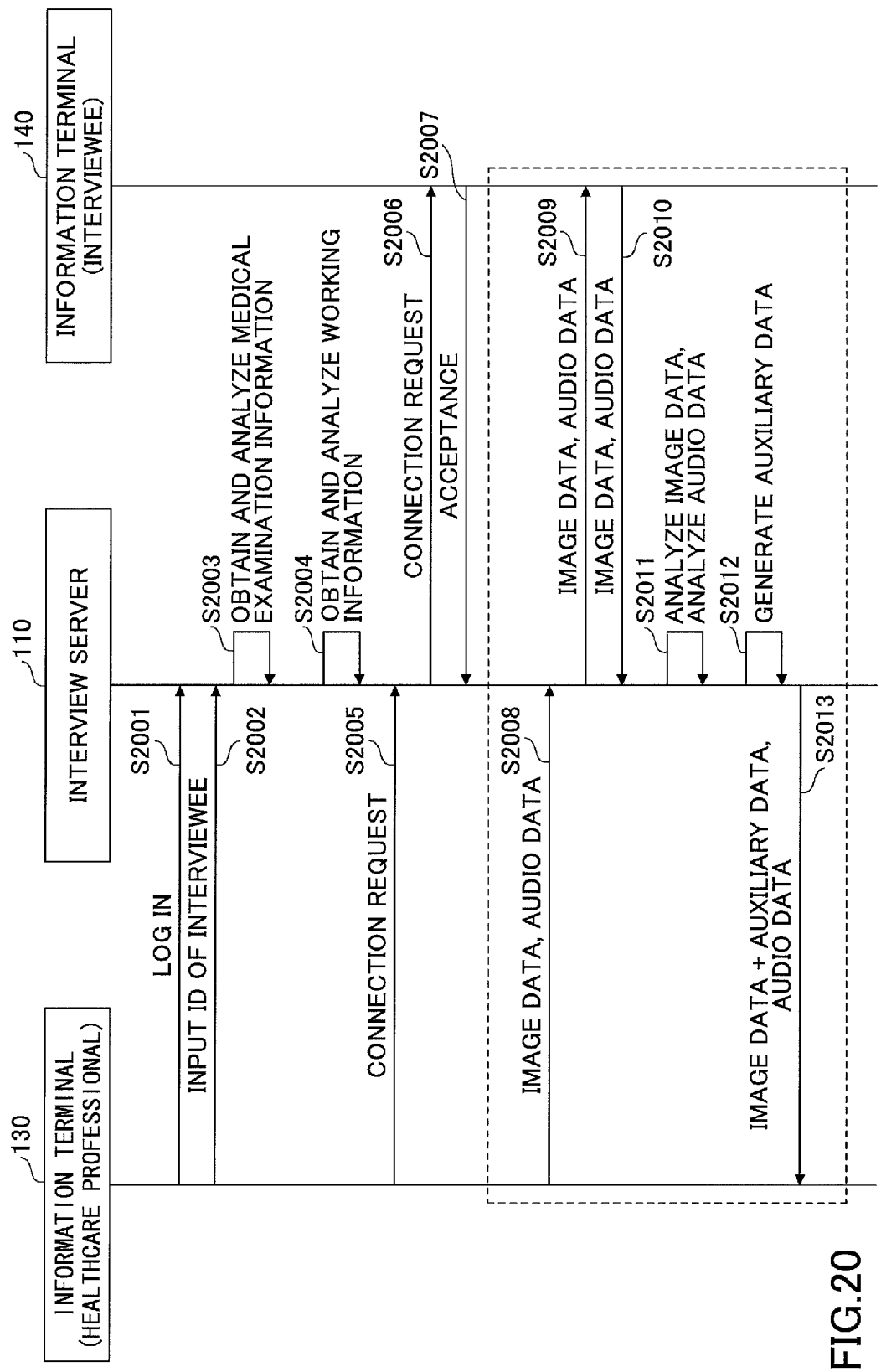
FIG. 20 is a sequence diagram showing a flow of a medical interview process in a medical interview system.

In the following, a flow of a medical interview process in the medical interview system 100 is described. FIG. 20 is a sequence diagram showing the flow of the medical interview process in the medical interview system 100.

As shown in FIG. 20, in step S2001, the healthcare professional 210 logs into the interview server 110 via the information terminal 130. If the log-in is successful, in step S2002, the healthcare professional 210 inputs an ID (such as an employee number) of the interviewee 220 as an object of a medical interview via the information terminal 130. The ID of the interviewee 220 input by the healthcare professional 210 is transmitted to the interview server 110.

In step S2003, the interview server 110 obtains medical examination information 500 that corresponds to the received ID of the interviewee 220 from the medical examination information DB 121. Further, the interview server 110 analyzes the obtained medical examination information 500 and derives graph area display information, health information, and display condition information.

In step S2004, the interview server 110 obtains working information 600 that corresponds to the received ID of the interviewee 220 from the working information DB 122. Further, the interview server 110 analyzes the obtained working information 600 and derives graph area display information and display condition information.

In step S2005, the healthcare professional 210 inputs an interview instruction to the information terminal 130. In accordance with this, the information terminal 130 transmits a connection request to the interview server 110, the connection request making a request for connection with the information terminal 140 to be used by the interviewee 220 when a medical interview with the interviewee 220 is to be held.

In step S2006, the interview server 110 that has received the connection request transmits the connection request to the information terminal 140 to be used by the interviewee 220.

In step S2007, in the information terminal 140 that has received the connection request from the interview server 110, the interviewee 220 performs an acceptance operation. In accordance with this, acceptance information is transmitted from the information terminal 140 to the interview server 110. As a result, the information terminal 130 and the information terminal 140 are connected via the interview server 110.

In step S2008, the information terminal 130 starts transmitting image data and audio data. In step S2009, the interview server 110 transmits the received image data and audio data to the information terminal 140. In accordance with this, the image data on the healthcare professional 210 is displayed as images and the audio data on the healthcare professional 210 is output as audio in the information terminal 140.

In step S2010, the information terminal 140 starts transmitting image data and audio data.

In step S2011, the interview server 110 analyzes the received image data and audio data. Further, in step S2012, the interview server 110 generates auxiliary data and superimposes the generated audio data on the image data.

In step S2013, the interview server 110 transmits the image data on which the auxiliary data is superimposed and the audio data to the information terminal 130. In accordance with this, the image data on the interviewee 220 on which the auxiliary data is superimposed is displayed as images and the audio data on the interviewee 220 is output as audio in the information terminal 130.

Thereafter, steps S2008 to S2013 are repeated until the healthcare professional 210 inputs a disconnection request via the information terminal 130. In accordance with these steps, the medical interview between the healthcare professional 210 and the interviewee 220 is realized.

From display content displayed in each field of the display screen 131, display content displayed in the mental information field 1901, the question field 1903, and the advice field 1905 depends on the image data and the audio data, so that the display content in these fields changes with the passage of time during the medical interview. Further, in the graph field 1904, item (1) "Became less energetic," item (2) "Became mentally unstable," item (4) "Became taciturn suddenly," and item (5) "Made complaints" also depend on the image data and the audio data, so that display content in these items changes with the passage of time during the medical interview.

By contrast, from display content displayed in each field of the display screen 131, display content displayed in the health information field 1902 does not depend on the image data or the audio data, so that the display content in the health information field 1902 remains the same regardless of the passage of time during the medical interview. Further, in the graph field 1904, item (3) "Became less interested in appearances," item (6) "Lost (gained) weight suddenly," item (7) "Increased amount of alcohol," and item (8) "Increased number of late arrivals and absence" do not depend on the image data or the audio data, so that display content in these items remains the same regardless of the passage of time during the medical interview.

<10. Conclusion>

As mentioned above, in the medical interview system 100 according to the present embodiment, the imaging unit 132 that photographs the healthcare professional 210 while facing a display direction of the display screen 131 as a photographing direction is disposed, the display screen 131 displaying image data on the interviewee 220 when a medical interview is held, auxiliary data necessary for the medical interview with the interviewee 220 is displayed in the display screen 131 where the image data on the interviewee 220 is displayed when the medical interview is held, and the auxiliary data necessary for the medical interview with the interviewee 220 is derived based on medical examination information and working information about the interviewee 220 and the image data and audio data about the interviewee 220 obtained during the medical interview.

In accordance with this, the healthcare professional 210 is capable of browsing the auxiliary data necessary for the medical interview with the interviewee 220 while facing the display screen 131. As a result, it is possible to maintain communication with the interviewee 220 in a virtual face-to-face state during the medical interview.

Second Embodiment

In the first embodiment mentioned above, the mental information field 1901, the health information field 1902, the question field 1903, the graph field 1904, and the advice field 1905 are disposed as fields that display auxiliary data. However, the present invention is not limited to this. For example, a part of the fields that display the auxiliary data may be hidden.

Further, in the first embodiment mentioned above, the auxiliary data is displayed only in the display screen 131 of the information terminal 130 used by the healthcare professional 210. However, the present invention is not limited to this. For example, a part of the auxiliary data may be displayed in the display screen 141 of the information terminal 140 used by the interviewee 220 such that the part of the auxiliary data is shared between the healthcare professional 210 and the interviewee 220. In the following, the second embodiment is described.

<1. Description of Display Screen>

Figure 21:
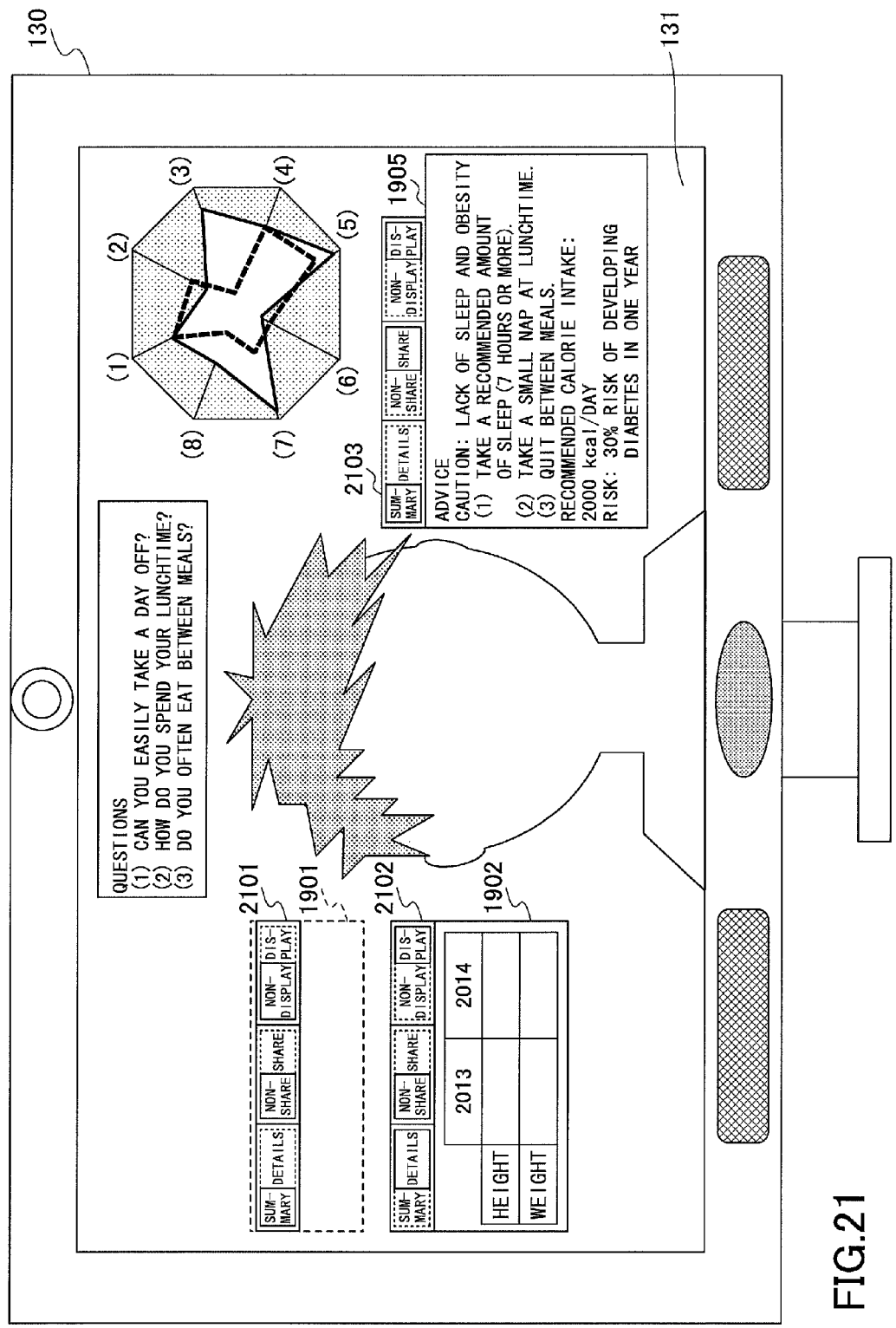
FIG. 21 is a diagram showing another display screen rendered in an information terminal used by a healthcare professional.

FIG. 21 is a diagram showing the display screen 131 rendered in the information terminal 130 used by the healthcare professional 210 in the medical interview system 100 according to the second embodiment. In addition, the same configurations as in the display screen 131 described with reference to FIG. 19 in the first embodiment will be given the same reference numerals and a description of such configurations will be omitted.

A difference from FIG. 19 is that a mental information field image is not displayed, the mental information field 1901 displays a tab, content of a health information field image is changed, and a health information field image and an advice field image are provided with a tab.

A tab 2101 shown in the mental information field 1901 is used to change display content of the mental information field image.

In the tab 2101, "Details" is used to display detailed information about information included in the mental information field image. When the "Details" of the tab 2101 is tapped, detailed information about information included in the mental information field image is displayed. By contrast, if "Summary" is tapped, it is possible to return from the detailed information to the mental information field image.

In the tab 2101, "Share" is used to share the mental information field image with the interviewee 220 by displaying the mental information field image also in the information terminal 140 used by the interviewee 220. When the "Share" of the tab 2101 is tapped, the mental information field image is also displayed in the information terminal 140 used by the interviewee 220. By contrast, if "Non-share" (to display only for the healthcare professional 210) is tapped, it is possible to return a shared mental information field image to a non-share state.

In the tab 2101, "Non-display" is used to hide the mental information field image in the information terminal 130 used by the healthcare professional 210. When the "Non-display" of the tab 2101 is tapped, the mental information field image is hidden. By contrast, if "Display" is tapped, it is possible to display the mental information field image again.

In FIG. 21, the "Non-display" of the tab 2101 is tapped in the mental information field 1901.

In the same manner, in the health information field 1902, a health information field image is provided with a tab 2102. In FIG. 21, "Details" of the tab 2102 is tapped. Specifically, the "Details" of the tab 2102 is tapped, so that detailed information about information included in the health information field image is displayed. The health information field image includes a change of a BMI value of the interviewee 220, so that the heights and the weights of the interviewee 220 used to calculate a BMI value before the change and a BMI value after the change are displayed as detailed information. Further, the health information field image includes a weight increase of the interviewee 220, so that the weight before the increase and the weight after the increase are displayed as detailed information.

In addition, if "Summary" is tapped while detailed information about information included in the health information field image is displayed, the health information field image will be displayed.

In the same manner, in the advice field 1905, an advice field image is provided with a tab 2103. In FIG. 21, "Share" of the tab 2103 is tapped. Specifically, the "Share" of the tab 2103 is tapped, so that an advice field image is also displayed in the information terminal 140 used by the interviewee 220 and the advice field image is shared between the healthcare professional 210 and the interviewee 220.

In addition, if "Non-share" is tapped while the advice field image is shared, the advice field image is not shared again, so that the advice field image will be displayed only in the information terminal 130 used by the healthcare professional 210.

<2. Flow of Data in Medical Interview System>

Figure 22:
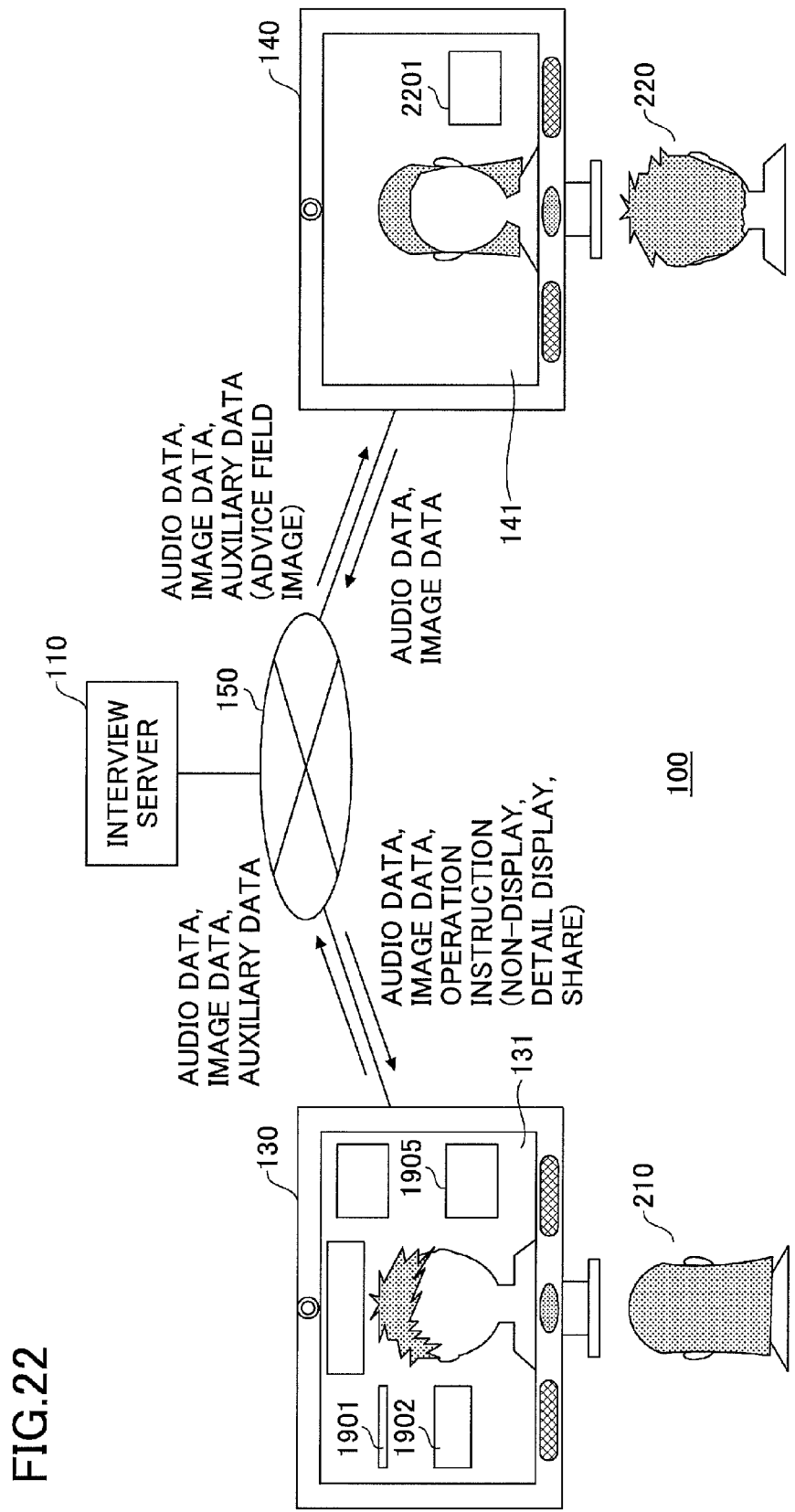
FIG. 22 is a diagram showing a flow of data in a medical interview system.

In the following, a relationship between the display screen 131 shown in FIG. 21 and a flow of data in the medical interview system 100 is described. FIG. 22 is a diagram showing a relationship between the display screen 131 shown in FIG. 21 and a flow of data in the medical interview system 100.

In the display screen 131 of the information terminal 130, if the "Non-display" of the tab 2101 is tapped, a non-display instruction to hide the mental information field image is transmitted from the information terminal 130 to the interview server 110 as an operation instruction as shown in FIG. 22. In response to this, the interview server 110 stops superimposing the mental information field image on image data as auxiliary data. Accordingly, the mental information field image is hidden in the mental information field 1901.

Further, if the "Details" of the tab 2102 is tapped, a detail display instruction to ask for detailed information about information included in the health information field image is transmitted from the information terminal 130 to the interview server 110 as an operation instruction as shown in FIG. 22. In response to this, the interview server 110 generates a health information field image using detailed information about the information included in the health information field image and superimposes the health information field image on image data as auxiliary data. Accordingly, the detailed information is displayed in the health information field 1902.

Further, if the "Share" of the tab 2103 is tapped, a share instruction to share the advice field image is transmitted from the information terminal 130 to the interview server 110 as an operation the interview server 110 superimposes the advice field image on image data to be transmitted to the information terminal 140 used by the interviewee 220. Accordingly, in the display screen 141 of the information terminal 140, the advice field image is displayed in an advice field 2201 in addition to the image data that indicates the healthcare professional 210. As a result, it is possible to share the advice field image between the healthcare professional 210 and the interviewee 220.

<3. Conclusion>

As mentioned above, in the medical interview system 100 according to the present embodiment, the display screen 131 of the information terminal 130 used by the healthcare professional 210 is provided with an instruction function to change display content of auxiliary data, and if an operation instruction to change display content of auxiliary data is input through the instruction function, the interview server 110 generates auxiliary data depending on the operation instruction, superimposes the generated auxiliary data on image data, and transmits resultant data to a destination depending on the operation instruction.

In accordance with this, it is possible to realize display/non-display, summary display/detail display, and share/non-share of auxiliary data depending on an operation instruction from the information terminal 130 used by the healthcare professional 210.

Third Embodiment

In the first embodiment, all information that can be displayed as auxiliary data is displayed. However, the present invention is not limited to this. For example, only information that matches a category specified by the healthcare professional 210 depending on a purpose of a medical interview may be displayed.

For example, if the healthcare professional 210 holds a medical interview as to lifestyle habits, information related to the lifestyle habits may be extracted and displayed as auxiliary data. Further, if the healthcare professional 210 holds a medical interview as to a medical examination result, information related to the medical examination information 500 may be extracted and displayed as auxiliary data.

In addition, when the healthcare professional 210 specifies a category depending on a purpose of a medical interview, the healthcare professional 210 may specify the category by selecting one of categories in the display screen 131, the categories being displayed in advance in a selectable manner. Alternatively, the healthcare professional 210 may specify the category by inputting a predetermined keyword.

Figure 23:
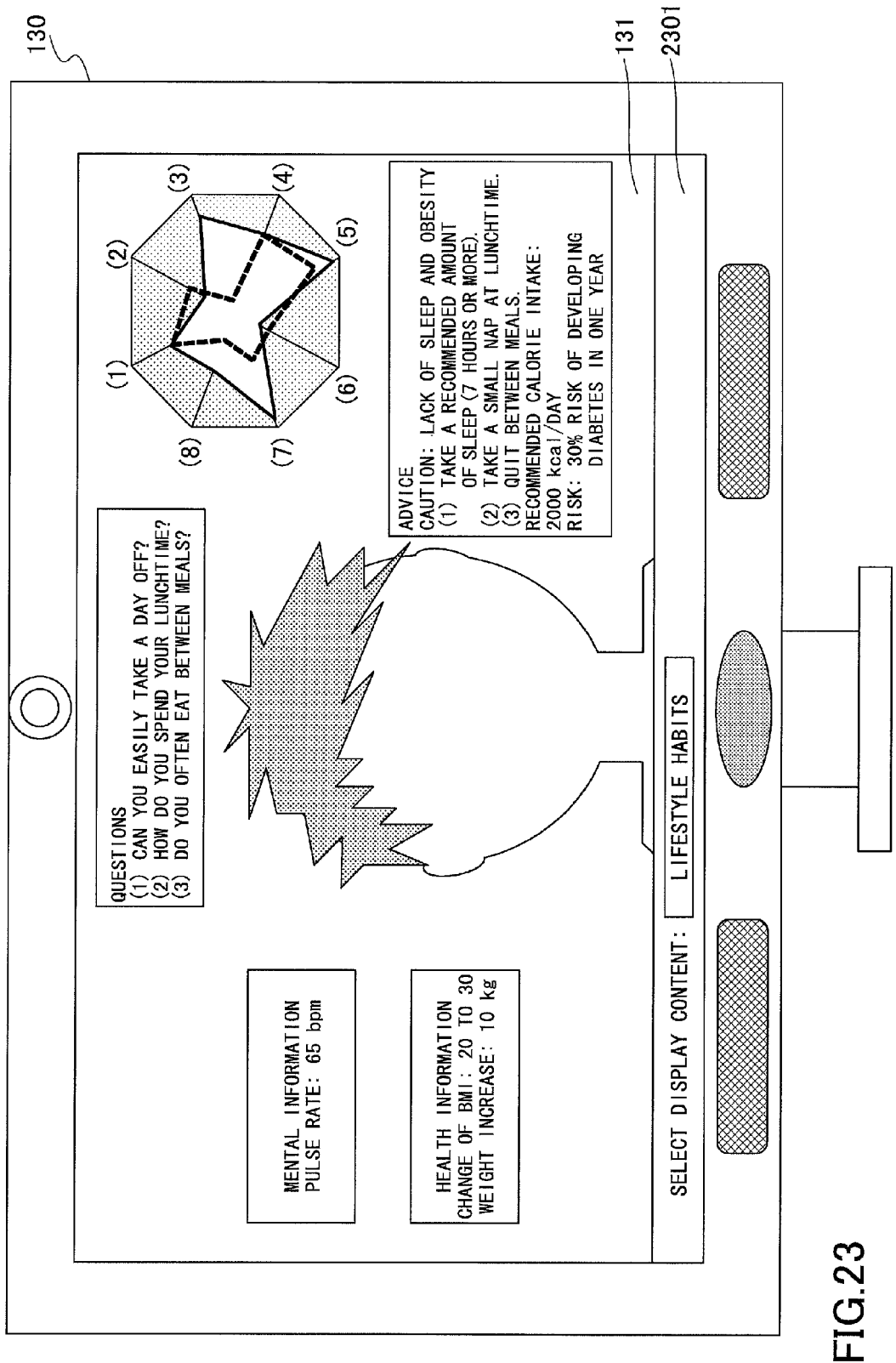
FIG. 23 is a diagram showing another display screen rendered in an information terminal used by a healthcare professional.

FIG. 23 is a diagram showing the display screen 131 that displays only information that matches the category specified by the healthcare professional 210 depending on the purpose of a medical interview. In FIG. 23, an input field 2031 to input a category is disposed in a lower portion of the display screen 131. The healthcare professional 210 may select display content by inputting a category in the input field 2031.

In FIG. 23, "lifestyle habits" is input in the input field 2031. As shown in FIG. 23, when the "lifestyle habits" is input in the input field 2031 as a category, an operation instruction to specify the category is transmitted to the interview server 110.

In response to this, the interview server 110 extracts information related to the "lifestyle habits" and generates auxiliary data.

As a result, the healthcare professional 210 can browse only information that matches the purpose of a medical interview and smoothly conduct the medical interview.

Fourth Embodiment

In the first to third embodiments described above, the interview server 110 generates auxiliary data. However, the present invention is not limited to this. For example, information necessary to generate auxiliary data may be stored in the information terminal 130 used by the healthcare professional 210. In accordance with this, it is possible to construct a medical interview system suitable for a communication environment.

Figure 24:
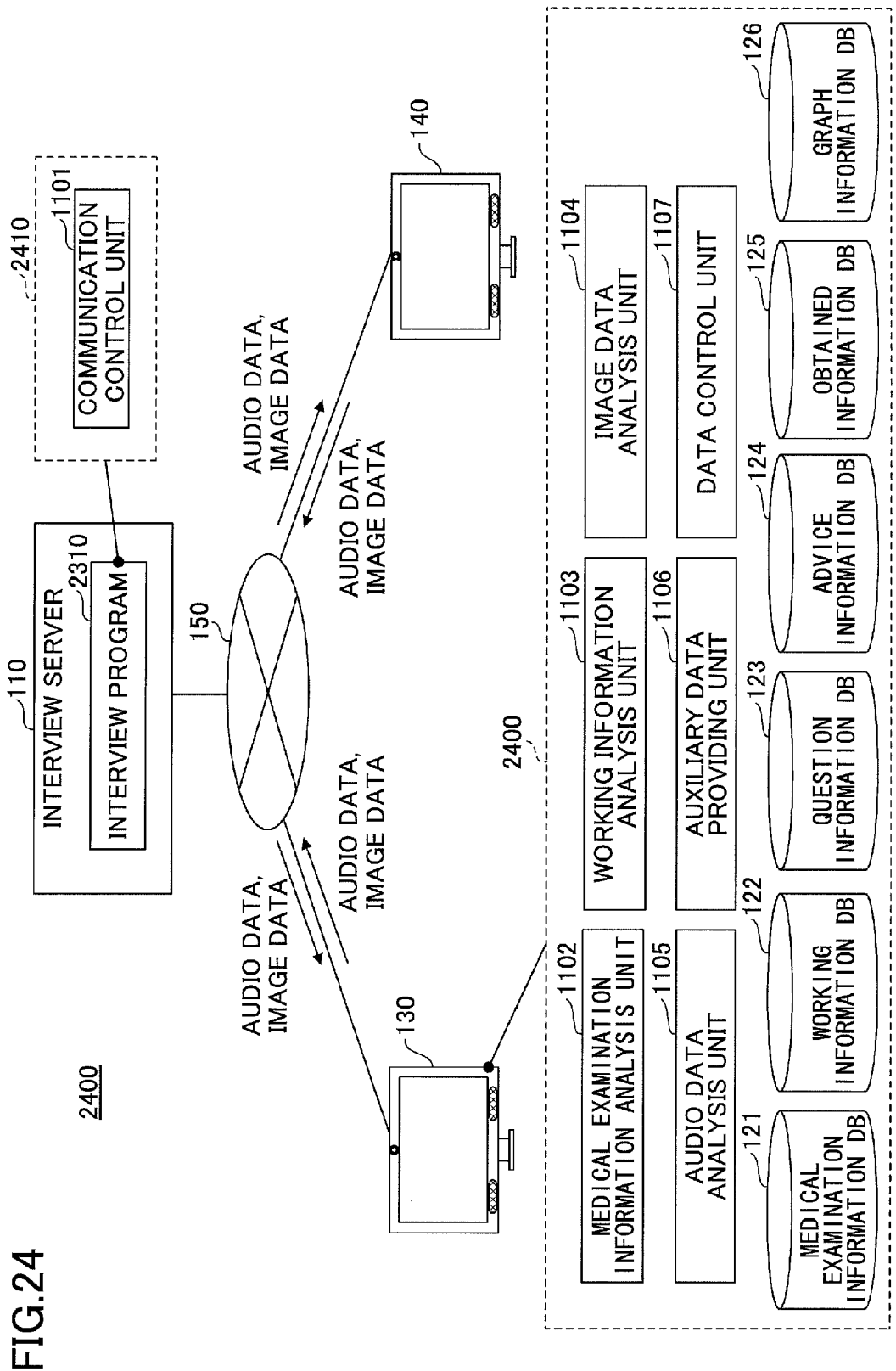
FIG. 24 is a diagram showing another medical interview system.

FIG. 24 is a diagram showing a medical interview system 2400 according to the fourth embodiment. The same configurations as in the medical interview system 100 described with reference to FIG. 1 in the first embodiment will be given the same reference numerals and a description of such configurations will be omitted.

A difference from FIG. 1 is that among functions and DBs included in the interview server 110, functions and DBs other than the communication control unit 1101 are disposed on the information terminal 130. In accordance with this, it is not necessary to transmit or receive auxiliary data between the interview server 110 and the information terminal 130.

In addition, assignment of functions shown in FIG. 24 is only an example and another assignment different from FIG. 24 may be employed. For example, a part of the image data analysis unit 1104 (the beat analysis unit 1401, the facial expression analysis unit 1402, the sentiment analysis unit 1403, the behavior analysis unit 1404, and the appearance analysis unit 1405) may be disposed on the information terminal 140 used by the interviewee 220. Further, a part of the audio data analysis unit 1105 (the time analysis unit 1601, the conversation analysis unit 1602, and the tone analysis unit 1603) may be disposed on the information terminal 140 used by the interviewee 220.

Fifth Embodiment

In the first to fourth embodiments described above, a pulse rate of the interviewee 220 is calculated per unit time based on image data. However, the present invention is not limited to this. The interviewee 220 may wear a pulse sensor and data detected by the pulse sensor may be transmitted to the interview server 110.

Further, the interviewee 220 may wear a sensor for obtaining biological data other than a pulse rate and an output of the sensor may be used to generate auxiliary data.

In addition, the present invention is not limited to configurations mentioned in the above-mentioned embodiments and other elements may be combined. These aspects may be changed without departing from the scope of the present invention and can be set appropriately depending on a form of application.

Further, the following configurations are described.

An interview system including:

a first information terminal used by an interviewer;

a server system having one or more server devices and controlling bidirectional communication of image data and audio data between the first information terminal and a second information terminal used by an interviewee;

a calculation unit that analyzes the image data and the audio data on the interviewee received from the second information terminal and calculates difference information that indicates a difference between a current state of the interviewee and a past state of the interviewee;

an image generation unit that superimposes the difference information on the image data received from the second information terminal, such that the difference information is displayed around a field where an image of the interviewee is placed; and a control unit that controls the image data on which the difference information is superimposed by the image generation unit and the audio data received from the second information terminal to be output in the first information terminal.

An interview method in an interview system including a first information terminal used by an interviewer and a server system having one or more server devices and controlling bidirectional communication of image data and audio data between the first information terminal and a second information terminal used by an interviewee; the interview method including:

analyzing the image data and the audio data on the interviewee received from the second information terminal and calculating difference information that indicates a difference between a current state of the interviewee and a past state of the interviewee;

superimposing the difference information on the image data received from the second information terminal, such that the difference information is displayed around a field where an image of the interviewee is placed; and controlling the image data on which the difference information is superimposed in the superimposing and the audio data received from the second information terminal to be output in the first information terminal.

Further, the present invention is not limited to these embodiments, and various variations and modifications may be made without departing from the scope of the present invention.

The present application is based on and claims the benefit of priority of Japanese Priority Application No. 2015-000717 filed on Jan. 6, 2015, the entire contents of which are hereby incorporated by reference.

What is claimed is:

1. An information processing system which includes one or more information processing devices and controls bidirectional communication of first image data, second image data, first audio data, and second audio data between a first information terminal used by a first user and a second information terminal used by a second user, the information processing system comprising:

a processor configured to:
analyze, via a calculation unit, the second image data and the second audio data on the second user received from the second information terminal,
calculate, via the calculation unit, difference information that indicates a difference between a current state of the second user and a past state of the second user;
superimpose, via an image generation unit, the difference information on the second image data received from the second information terminal, such that the difference information is displayed around a field where an image of the second user is placed; and arranging and displaying additional fields around where the image of the second user is displayed, the additional fields being at least one of a question field and an advice field, and a transmission unit configured to transmit, to the first information terminal, the second image data on which the difference information is superimposed by the image generation unit and the second audio data received from the second information terminal.

2. The information processing system as claimed in claim 1, wherein the first image data received from the first information terminal is obtained by an imaging unit disposed in proximity to a display screen of the first information terminal, the display screen displaying the second image data on which the difference information is superimposed by the image generation unit, the imaging unit facing a display direction of the display screen as a photographing direction.

3. The information processing system as claimed in claim 1, wherein the image generation unit is configured to extract, from the difference information, category information that matches a category specified by the first information terminal, and superimposes the category information on the second image data received from the second information terminal.

4. The information processing system as claimed in claim 1, wherein the image generation unit is configured to superimpose the difference information on the second image data received from the second information terminal, such that the difference information is classified into a plurality of fields and displayed therein, the plurality of fields being provided around the field where the image of the second user is placed.

5. The information processing system as claimed in claim 4, wherein the image generation unit is configured to superimpose the difference information on the second image data received from the second information terminal, the difference information being classified into one of the plurality of fields specified for display by the first information terminal.

6. The information processing system as claimed in claim 4, wherein
the image generation unit is configured to superimpose the difference information on the first image data received from the first information terminal, the difference information being classified into one of the plurality of fields specified for sharing by the first information terminal, such that the difference information is displayed around a field where an image of the first user is placed, and the transmission unit is configured to transmit, to the second information terminal, the first image data on which the difference information is superimposed by the image generation unit, the difference information being classified into the one of the plurality of fields specified for sharing, and the first audio data received from the first information terminal.

7. The information processing system as claimed in claim 4, wherein if the first information terminal specifies display of detailed information in a predetermined field among the plurality of fields, the image generation unit superimposes original information on the second image data received from the second information terminal, the original information being used by the calculation unit in order to calculate the difference information classified into the predetermined field.

8. The information processing system as claimed in claim 1, further comprising:
a storage unit configured to store information indicating the past state of the second user, the information indicating past state of the second user being used by the calculation unit in order to calculate the difference information.

9. The information processing system as claimed in claim 1, wherein the question field is displayed above the image of the second user on the display.

10. The information processing system as claimed in claim 1, wherein the advice field is displayed at a side of the image of the second user on the display.

11. An information processing method in an information processing system which includes one or more information processing devices and controls bidirectional communication of image data and audio data between a first information terminal used by a first user and a second information terminal used by a second user, the information processing method comprising:
analyzing the image data and the audio data on the second user received from the second information terminal and calculating difference information that indicates a difference between a current state of the second user and a past state of the second user;

superimposing the difference information on the image data received from the second information terminal, such that the difference information is displayed around a field where an image of the second user is placed;

arranging and displaying additional fields around where the image of the second user is displayed, the additional fields being at least one of a question field and an advice field, and transmitting, to the first information terminal, the image data on which the difference information is superimposed in the superimposing and the audio data received from the second information terminal.

12. An information processing apparatus that controls bidirectional communication of image data and audio data between a first information terminal used by a first user and a second information terminal used by a second user, the information processing apparatus comprising:
a processor configured to:
analyze, via a calculation unit, the image data and the audio data on the second user received from the second information terminal and calculates difference information that indicates a difference between a current state of the second user and a past state of the second user;

superimpose, via an image generation unit, the difference information on the image data received from the second information terminal, such that the difference information is displayed around a field where an image of the second user is placed; and arrange and display additional fields around where the image of the second user is displayed, the additional fields being at least one of a question field and an advice field, and a transmission unit that transmits, to the first information terminal, the image data on which the difference information is superimposed by the image generation unit and the audio data received from the second information terminal.

* * * * *